United States Patent
Sim

(10) Patent No.: US 9,669,067 B2
(45) Date of Patent: Jun. 6, 2017

(54) USE OF DES-ASPARTATE-ANGIOTENSIN I IN INFLAMMATION-RELATED PATHOLOGIES AND DISEASES

(71) Applicant: Meng Kwoon Sim, Singapore (SG)

(72) Inventor: Meng Kwoon Sim, Singapore (SG)

(73) Assignee: SimPharma Pte Ltd, Singapore (SG)

( * ) Notice: Subject to any disclaimer, the term of this patent is extended or adjusted under 35 U.S.C. 154(b) by 109 days.

(21) Appl. No.: 14/558,435

(22) Filed: Dec. 2, 2014

(65) Prior Publication Data
US 2015/0164979 A1 Jun. 18, 2015

Related U.S. Application Data

(62) Division of application No. 13/703,106, filed as application No. PCT/SG2011/000204 on Jun. 8, 2011, now Pat. No. 8,980,250.

(60) Provisional application No. 61/397,609, filed on Jun. 14, 2010.

(51) Int. Cl.
| | | |
|---|---|---|
| A61K 35/12 | (2015.01) | |
| A61K 38/08 | (2006.01) | |
| A61K 35/545 | (2015.01) | |
| A61K 45/06 | (2006.01) | |
| A61N 5/10 | (2006.01) | |

(52) U.S. Cl.
CPC .......... *A61K 38/085* (2013.01); *A61K 35/545* (2013.01); *A61K 45/06* (2013.01); *A61N 5/10* (2013.01)

(58) Field of Classification Search
CPC .................................................. A61K 38/085
See application file for complete search history.

(56) References Cited

U.S. PATENT DOCUMENTS 8,034,781 B2 * 10/2011 Tallant ................. A61K 38/085
424/1.69

OTHER PUBLICATIONS

Rodgers et al., Phase I/II dose escalation study of angiotensin 1-7 [A(1-7)] administered before and after chemotherapy in patients with newly diagnosed breast cancer. Cancer Chemotherapy Pharmacology, vol. 57, No. 5 (May 2006) pp. 559-568.*
Heringer-Walther et al., Angiotensin-(1-7) stimulates hematopoietic progenitor cells in vitro and in vivo. Haematologica, vol. 94 (Jun. 2009) pp. 857-860.*
Tsutsumi and Neckers (2007) "Extracellular heat shock protein 90: A role for a molecular chaperone in cell motility and cancer metastasis" Cancer Sce. 98:1536-1539 (2007).
Ulich et al., (1991) "Intratracheal Injection of Endotoxin and Cytokines: II. Interleukin-6 and Transforming Growth Factor Beta Inhibit Acute Inflammation" Am. J. Pathol., 138:1097-1101.
Wataru et al., (2004) "Oxidative stress and delayed-onset muscle damage after exercise" Free Radic. Biol. Med., 37:480-487.
Wen et al., (2004) "Reduction of infarct size by orally administered des-aspartate-angiotensin I in the ischemic reperfused rat heart" Regul Pept., 120:149-153.
Wu and Zhou, (2009) "Inflammation: A driving force speeds cancer metastasis" Cell Cycle 8:3267-3273.
Zhou et al., (2008) "Protocatechuic aldehyde suppresses TNF-α-induced ICAM-1 and VCAM-1 expression in human umbilical vein endothelial cells" Eur. J. Pharmacol., 513:1-8.
Poitout et al., (1996) "Insulin-secreting cell lines: classification, characteristics and potential applications." Diabetes Metab. 22:7-14 (Abstract only).

* cited by examiner

*Primary Examiner* — Kara Johnson
(74) *Attorney, Agent, or Firm* — Markey IP Law LLC; James G. Markey; Graham C. Alig

(57) ABSTRACT

The present disclosure generally relates to the use of des-aspartate-angiotensin I and/or its derivatives in medicine. In particular, the present invention relates to the use of des-aspartate-angiotensin I and/or its derivatives for the treatment and/or prophylaxis of inflammatory diseases or pathologies, for inducing anti-inflammatory actions and/or reducing inflammation, and/or for treatment of inflammation-related conditions.

18 Claims, 19 Drawing Sheets

USE OF DES-ASPARTATE-ANGIOTENSIN I IN INFLAMMATION-RELATED PATHOLOGIES AND DISEASES

CROSS REFERENCE TO RELATED APPLICATIONS

The present application is a divisional application under 35 U.S.C. §120 of application Ser. No. 13/703,106, filed on Dec. 27, 2012, which was issued as U.S. Pat. No. 8,980,250 and which is a 35 U.S.C. §371 National Phase conversion of PCT/SG2011/000204, filed Jun. 8, 2011, which claims benefit of U.S. Provisional Application No. 61/397,609, filed Jun. 14, 2010, the disclosure of which is incorporated herein by reference. The PCT International Application was published in the English language.

FIELD OF INVENTION

The present invention relates to the treatment of pathologies and diseases that are inflammatory in nature. The treatment is practiced by the administration of des-aspartate-angiotensin I or its derivatives to a subject in need of such a treatment. The present invention further contemplates the use of des-aspartate-angiotensin I or its derivatives in the treatment and/or prophylaxis of cellular inflammation arising from chemical, physical, and biological insults.

BACKGROUND OF THE INVENTION

Des-aspartate-angiotensin I is an endogenous angiotensin peptide (Sim and Qiu, Regul. Pept., 111:179-182 (2002)). It is formed from angiotensin I by a specific aminopeptidase present in blood vessels and the hypothalamus (Sim, Biochem. Pharmacol., 45:1524-1527 (1994); Sim et al., Biochem. Pharmacol., 48:1043-1046)). Our previous studies have shown that des-aspartate-angiotensin I exerts useful cardiovascular and renal actions (U.S. Pat. Nos. 5,773,415; 6,100,237; US2003/0086920 A1; U.S. Pat. No. 6,589,938 B2) attenuates insulin resistance in type 2 diabetic animals and combats viral infection (Sim et al., Endocrinology, 148:5925-5932 (2008); PCT No. WO 2007/030082 A1). Earlier studies have also shown that des-aspartate-angiotensin I acts as an agonist on the angiotensin AT1 receptor and that its actions were indomethacin sensitive (Sim and Soh, Eur. J. Pharmacol., 284:215-219 (1995); Sim and Chai, Br. J. Pharmacol., 117:1504-1506 (1996); Min et al., Regul Pept., 95:93-97 (2000); Wen et al., Regul Pept., 120:149-153 (2004)). The present invention identifies a specific interaction between des-aspartate-angiotensin I and the angiotensin AT1 receptor in which only prostaglandins E2 and I2 (PGE2 and PGI2) are produced by the enzymatic action of COX1. PGE2 and PGI2, so produced, mediate the biological actions of des-aspartate-angiotensin I. PGE2 acts on its receptor, which exists as four subtypes (EP1 to EP4). It produces a variety of responses which blur the line between it being categorized as a proinflammatory or anti-inflammatory molecule, (Fraser, Int. Rev. Immunol., 27:320-350 (2008)). PGE2 and PGI2 are involved in inflammation-related vasodilation and synergize with other proinflammatory mediators to increase vascular permeability and promote edema (Khanapure et al., Curr. Top. Med. Chem., 7:311-340 (2007)). Current understanding of the roles of COX1 and COX2 in physiology, pathophysiology and inflammation are also equivocal and there are conditions where either COXs could be involved in inflammation (Rouzer and Marnett, J. Lipid Res., 50:S29-S34 (2009)). In the context of the dual pro- and anti-inflammatory roles of PGE2 and PGI2, and COX1 and COX2, this invention shows a specific novel pathway in which des-aspartate-angiotensin I acts on the angiotensin AT1 receptor and activates only COX1 to produce PGE2 and PGI2. In the setting of diseases and pathologies that are inflammatory in nature, it was surprisingly discovered that the PGE2 and PGI2 so produced attenuate the symptoms of the diseases and pathologies.

Inflammation is a complex response to injurious stimuli and is mediated and influenced by pleiotropic cytokines. Hence, an earlier study by Rufaihah et al. wrongly concluded that the cardioprotective effect of des-aspartate-angiotensin I was due to its suppression of genes of pro-inflammatory cytokines IL-6, TGF-β and GM-CSF that were upregulated in the rat model of myocardial infarction (Rufaihah et al., Life Sci., 78:1341-1351 (2006)). Firstly, the cytokines IL-6, TGF-β and GM-CSF have been shown to exhibit anti-inflammatory properties. IL-6 is an anti-inflammatory cytokine and attenuates the production of TNF-α in inflammation (Ulich et al., Am. J. Pathol., 138:1097-1101 (1991); Denis, J. Leuko. Biol., 52:197-201 (1992)). This probably accounted for the absence of des-aspartate-angiotensin I effect on upregulated TNF-α gene in the first 7 days of Rufaihah's study. TGF-β is a potent anti-inflammatory cytokine; surviving mice with knockout TGF-β gene exhibit fulminating inflammatory lesions of the heart and other organs (Kulkarni and Karlsson, Am. J. Pathol., 143:3-9 (1993)). In addition, high level of TGF-β in cow milk has been shown to protect against inflammation in mice (Ozawa et al., J. Nutr., 139:69-75 (2009)). GM-CSF is highly pleiotropic and has been shown to exhibit anti-inflammatory actions in inflammatory gut diseases (Korzenik et al., N. Engl. J. Med., 352:2193-2201 (2005); Sainathan et al., Inflamm. Bowel Dis. 14:88-99 (2008)). Secondly, cytokine gene profile in the contralateral area of normal heart tissues was also affected by des-aspartate-angiotensin I especially TNF-α gene, which increased in level in des-aspartate-angiotensin I treated animals in Day 3. Thirdly, an increase in cytokine gene expression does not necessarily translate to protein expression of the cytokine. Therefore, Rufaihah's study does not teach that the actions of des-aspartate-angiotensin I are anti-inflammatory in the rat model of myocardial infarction. It, however, teaches that des-aspartate-angiotensin I exerts cardioprotective effects, which resulted in the gradual normalization of upregulated gene expression of IL-6, TGF-β, and CM-CSF.

The ability of des-aspartate-angiotensin I to combat diseases bearing different pathologies and in different organs is not only unique but intriguing. While researching the mechanisms of its multi-disease action, it was surprisingly found that DAA-I specifically halts the early events of inflammation. These anti-inflammatory actions were useful in inflammatory diseases arising from chemical, physical, and biological insults and/or causes.

SUMMARY OF THE INVENTION

The present invention addresses the problems above and provides new uses and/or method(s) for des-aspartate-angiotensin I and its derivatives. In particular, des-aspartate-angiotensin I and its derivatives are used for the treatment and/or prevention of inflammatory diseases and their symptoms. The treatment and/or prevention consist(s) of administering to a subject or human patient, in need of such treatment or prevention, an effective amount of des-aspartate-angiotensin I or its derivatives for a time and under conditions sufficient for the onset of inflammatory symptoms to be prevented, inhibited or delayed or the symptoms of the inflammation to be ameliorated. The inflammatory diseases include (but are not restricted to):

(1) diseases resulting from exposure to a vesicant or toxic chemical that causes systemic and/or localized inflammation;
(2) skeletal muscle damage that resulted from unaccustomed or excessive strenuous use or exercise;
(3) heat stroke that resulted from exposure to high ambient temperature or strenuous exercise;
(4) Parkinson's disease or degenerative brain conditions resulting from inflammation;
(5) diseases that are caused by over-expressed proinflammatory cytokines such as, but no restricted to, TNF-α;
(6) diseases that are caused by over-production of ROS such as, but not restricted, $H_2O_2$;
(7) diseases that are caused by LPS or gram negative bacteria that produce LPS;
(8) malignant and invasive growth, tumor, tumor metastasis or cancer;
(9) inflammatory diseases that are ameliorated or cured by the agonistic action of des-aspartate-angiotensin I and/or its derivative on the angiotensin AT1 receptor in which PGE2 and PGI2 are produced by COX1.

Another aspect of the present invention provides a composition for use in the treatment and/or prevention of inflammatory diseases and their symptoms in a subject in need of such treatment and/or prevention comprising administering to the patient an effective amount of des-aspartate-angiotensin I or its derivatives.

In yet another aspect, the present invention provides a method or composition for use in the treatment and/or prevention of inflammatory diseases and their symptoms in a subject in need of such treatment and/or prevention comprising administering to the patient an effective amount of des-aspartate-angiotensin I or its derivatives and at least one pharmaceutically acceptable carrier, excipient, diluent and/or adjuvant.

There is also provided a kit comprising des-aspartate-angiotensin I or its derivatives, wherein the kit is for the treatment and/or prevention of inflammatory diseases and their symptoms.

Des-aspartate-angiotensin I, its derivatives or the pharmaceutical composition according to the invention may be administered in solid or liquid form.

Further, des-aspartate-angiotensin I, its derivatives or the pharmaceutical composition may be administered in conjunction with at least one pharmaceutical agent. The at least one pharmaceutical agent is an angiotensin converting enzyme inhibitor, an angiotensin receptor antagonist, and/or at least one type of stem cell.

BRIEF DESCRIPTION OF THE DRAWINGS

The present invention will be readily understood by the following detailed description in conjunction with the accompanying drawings. In some of the drawings (FIGS. 1-19), des-aspartate-angiotensin I was abbreviated as DAA-I, and half sulfur mustard as HSM.

FIG. 1 illustrates the effects of orally administered DAA-I on T1-α protein in BALF of HSM inoculated mice. BALF extraction was performed on anesthetized animals on Day 1, 7 and 14 post-HSM inoculation. BALF samples were freeze dried and re-suspended in 100 uL of PBS. 200 micrograms of protein from each sample were subjected to SDS-PAGE, transferred to polyvinylidene difluoride sheets, incubated with anti-T1-a polyclonal primary antibody (1:1000), washed and incubated with anti-mouse secondary antibody (1:10000). Upper panel: Representative Western blots of T1-α protein in BALF. Naïve (water: naive mice administered water. Vehicle (water: mice inoculated with vehicle (25 uL of 50% ethanol) and treated with water. HSM (water: mice inoculated with HSM and treated with water. HSM (DAA): mice inoculated with HSM and treated with 75 nmole/kg DAA-1. Note that T1-α protein was undetectable in both normal and vehicle treated animals. Lower panel: Densitometry readings for T1-α protein. Values represent mean density±SEM of 6 animals. Significance between groups was assessed by one way ANOVA with post-hoc Tukey test. *Significantly different from the corresponding value of HSM treated mice that were administered water ($p<0.05$).

FIG. 2 illustrates the effects of DAA-I on superoxide production in lungs of HSM inoculated mice. Lungs from each group were excised, rinsed in PBS and snap frozen in liquid nitrogen, before mounting in TissueTek medium. 20 μm sections were then cut using a cryostat. Lung cryosections were fixed in −20° C. acetone before addition of 10 pmole dihydroethidium Upper panel Ethidium fluorescence of lung cryosections. Fluorescence was analysed using a fluorescence microscope and arbitrary density values were tabulated. Naïve (Water): naïve mice administered water. Vehicle (water): mice inoculated with vehicle (25 uL of 50% ethanol) and treated with water. HSM (Water): mice inoculated with HSM and treated with water. HSM (DAA): mice inoculated with HSM and treated with 75 DAA-1. Lower panel: Fluorescence densitometry of cryosections. *Significantly different ($p<0.05$, ANOVA post hoc Tukey test) from the value of naïve animals. #Significantly different from the corresponding value of HSM inoculated animals that were administered water.

FIG. 3 illustrates the effects of DAA-I on overexpressed ICAM1 protein in lungs of HSM-inoculated mice. Upper panel: Representative Western blots of ICAM-1 protein in lung extract. Naive (water): Naive mice administered water. Vehicle (water): mice inoculated vehicle (25 uL of 50% ethanol) and administered water. HSM (water): mice inoculated with 0.28 mg/kg HSM and administered water. HSM (DAA-I): mice inoculated with 0.28 mg/kg HSM and administered 75 nmole/kg DAA-I. Lower panel: Densitometry readings for ICAM-1. Basal ICAM-1 was detected in lungs of naive mice values represent mean density±SEM of 3 animals. *Significantly different from the value of naive mice. #Significantly different from the corresponding value of HSM-inoculated mice that were administered Water.

FIG. 4 illustrates the effects of DAA-I on pulmonary MPO activity in HSM-inoculated mice. Naive (water): naive mice administered water. Vehicle (water): mice inoculated vehicle (25 uL of 50%) and administered water. HSM (water): mice inoculated with 0.28 mg/kg HSM and administered water. HSM (DAA-I): mice inoculated with 0.28 mg/kg HSM and administered 75 nmole/kg DAA-I. Each value represents the mean±SEM of 6 individual animals. *Significantly different from the value of naive animals. #Significantly different from the corresponding value of HSM.

FIG. 5 illustrates the effects of DAA-I on gp91-phox protein in lungs of HSM-inoculated mice. Upper panel: Representative Western blots of gp91-phox and actin. Lower panel: Densitometry readings of the Western blots. Naive (water): Naive mice administered water. Vehicle (water) mice inoculated vehicle (25 uL of 50% ethanol) and administered water. HSM (water): mice inoculated with 0.28 mg/kg HSM and administered water. HSM (DAA-1): mice inoculated with 0.28 mg/kg HSM and administered 75 nmole/kg DAA-I. Each value represents the mean±SEM of 3 animals. *Significantly different from the value of naive animals. #Significantly different from the corresponding value of HSM-inoculated animals that were administered water.

FIG. 6 illustrates the effects of DAA-I on PGE2 and PGI2 concentration in lung supernatant of HSM-inoculated mice. Naïve (water): naive mice administered water. Vehicle (water): mice inoculated vehicle (25 μL of 50% ethanol) and administered water. HSM (water): mice inoculated with 0.28 mg/kg HSM and administered water. HSM (DAA): mice inoculated with 0.28 mg/kg HSM and administered 75 nmole/kg DAA-I. Each value represents the mean±SEM of 3 animals. Upper histograms: Concentration of pulmonary PGE2. Lower histograms. Concentration of –6-ketoPGF1α, a stable metabolite of PGI2 (surrogate measurement of PGI2). *Significantly different from the value of vehicle animals. #Significantly different from the corresponding value of HSM-inoculated animals that were administered water.

FIG. 7 illustrates the effects of DAA-I and losartan on the survival of HSM-inoculated mice. Male Balb1/c mice were randomly divided into 7 groups of 10 animals per group. Animals were anesthetized with intraperitoneal avertin (8 mg/25 g) before intranasal inoculation with 0.28 mg HSM dissolved in 25 uL of 50% ethanol. Groups 25 were orally administered, by gavage, 75 nmole/kg DAA-I dissolved in 0.1 mL water daily for 14 days. Group 1 animals were similarly administered 0.1 mL water daily for 14 days. In addition, groups 2-6 were administered daily 0.5 nmole/kg, 1 nmole/kg, 0.34 μmole/kg and 0.64 μmolekg losartan, respectively, dissolved in 0.1 mL PBS daily for 14 days. Group 7 mice were administered only 0.5 nmole/kg losartan. Mice survival was monitored for 21 days.

Note that Losartan, at 0.5 nmole/kg, had no effect on the survival of the HSM-inoculated mice (unfilled histogram) However, when administered concurrently with DAA-I, it blocked the action of DAA-I indicating that DAA-I exerts its protective action via the angiotensin AT1 receptor.

Figure 8:
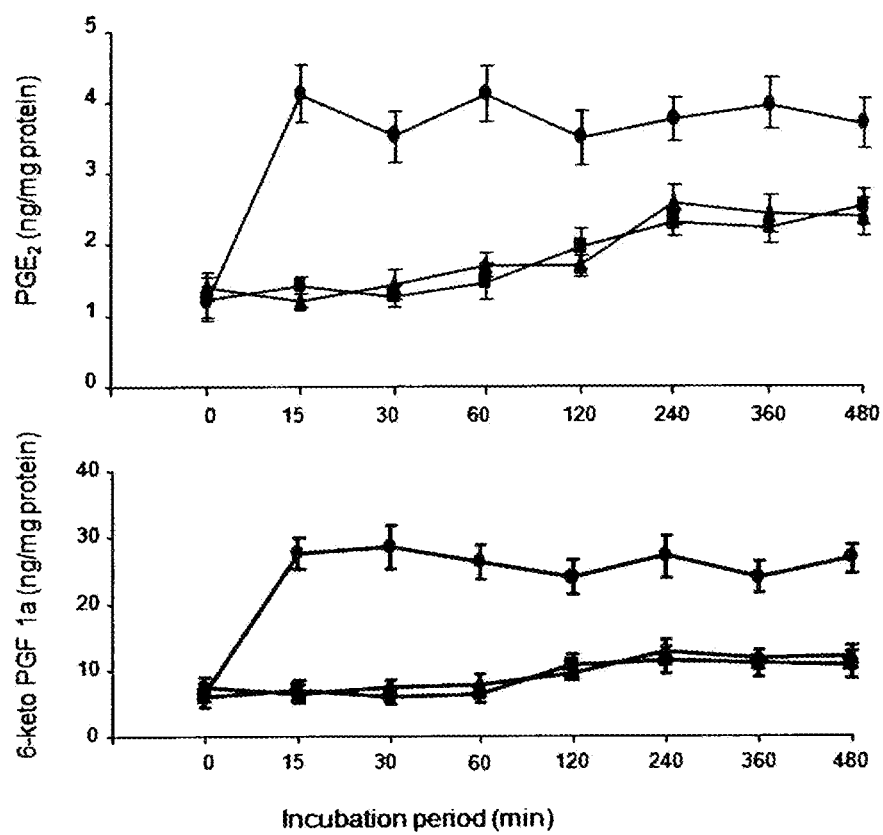

FIG. 8 shows that at a dose of $10^{-10}$ M, DAA-I specifically induced the production of PGE2 (upper panel) and PGI2 (lower panel) in HUVEC. At a higher concentration of $10^{-5}$ M, DAA-I was less effective and mimicked the action of angiotensin II.

FIG. 8 illustrates the effects of des-aspartate-angiotensin I and angiotensin II on the production of PGE2 and PGI2 in human umbilical vein endothelial cells. Cells were incubated with $10^{-10}$M des-aspartate-angiotensin (•), $10^{-5}$ M des-aspartate-angiotensin I (■) and $10^{-7}$M angiotensin II (▲) for 480 min Data are expressed as mean±SEM of three separate experiments performed in duplicate. All values at 15 and post 15 min stimulation were significantly different from the unstimulated (0 min) value (p<0.05, ANOVA, post hoc Tukey test).

Note that PGI2 is unstable and its stable metabolite 6-keto PGF 1α was determined as a surrogate. At a concentration of $10^{-5}$M, des-aspartate-angiotensin mimics the action of angiotensin II. This concentration is 100,000 times the effective dose.

Figure 9:
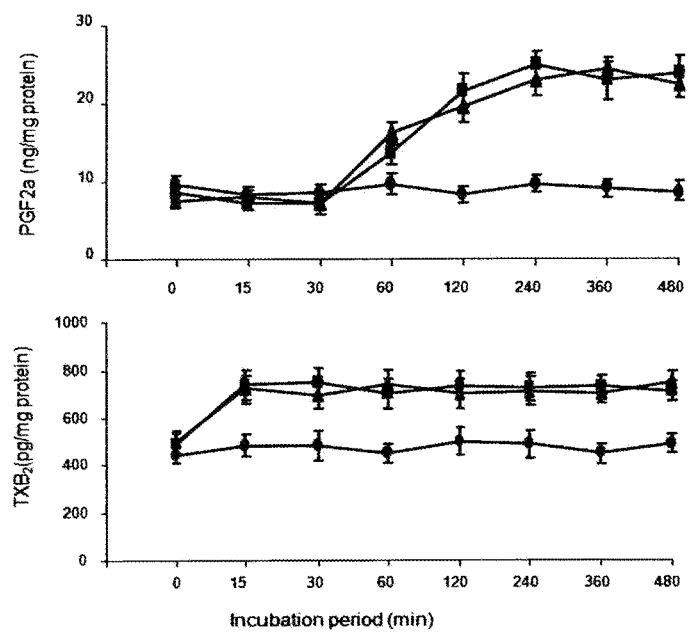

FIG. 9 shows that at a dose of $10^{-10}$ M, DAA-I had no effect on the basal production of PGF2α (upper panel) and thromboxane A2 (lower panel) in HUVEC. At a higher concentration of $10^{-5}$ M, DAA-I mimicked angiotensin II in inducing the production of PGF2α and TXA2.

FIG. 9 illustrates the effects of des-aspartate-angiotensin I and angiotensin II on the production of PGF2α and TXB2 in human umbilical vein endothelial cells. Cells were incubated with $10^{-10}$ M des-aspartate-angiotensin I (•), $10^{-5}$M des-aspartate-angiotensin I (■) and $10^{-7}$M angiotensin II (▲) for 480 min. Data are expressed as mean±SEM of three separate experiments performed in duplicate. $10^{-10}$ M des-aspartate-angiotensin I had no effects on the basal production of TXB2. i.e. all values at 15 and post 15 min stimulation were not significantly different from the unstimulated (0 min) value.

Note that TXA2 is unstable and its stable metabolite TXB2 was determined as a surrogate. At a concentration of $10^{-5}$M, des-aspartate-angiotensin I mimics the action of angiotensin II. This concentration is 100,000 times the non-effective dose.

Figure 10:
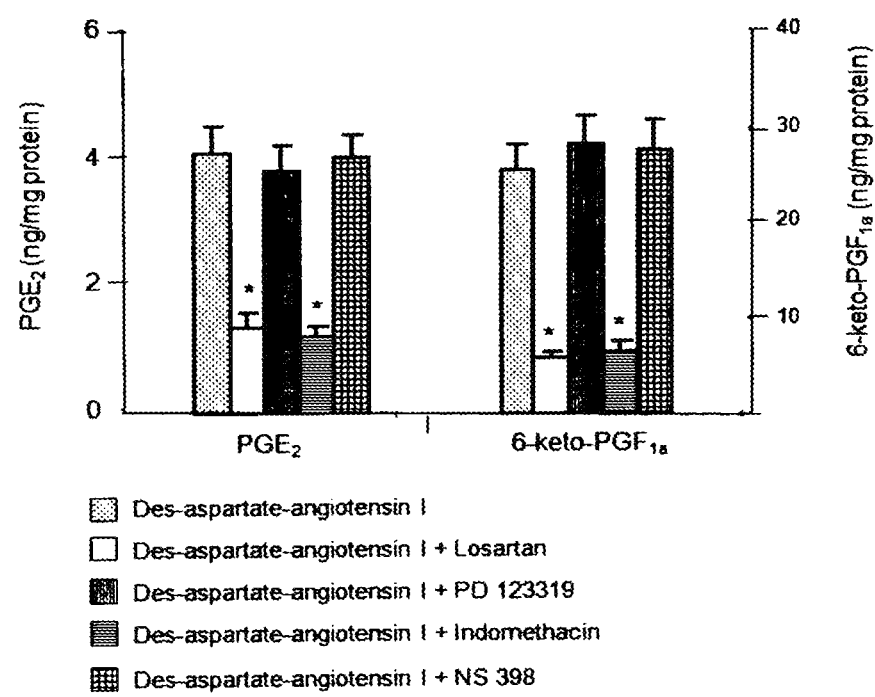

FIG. 10 shows that the ability of DAA-I to induce production of PGE2 and PGI2 in HUVEC was blocked by losartan and indomethacin, and not by PD123319 and NS 398. Losartan is an angiotensin AT1 receptor blocker and PD123319 is an angiotensin AT2 receptor blocker. Indomethacin is an inhibitor of both COX1 and COX2, and NS 398 is a specific inhibitor of COX2. Thus, the results show that DAA-I acted on the angiotensin AT1 receptor and stimulated COX1 leading to the production of PGE2 and PGI2.

FIG. 10 illustrates the effect of angiotensin receptor antagonists and inhibitors of cyclooxygenase on des-aspartate-angiotensin-I-stimulated synthesis of PGE2 and PGI2 in human umbilical vein endothelial cells. Cells were pre-incubated in the presence or absence of angiotensin receptor antagonists (1 μM losartan or PD 123319) or inhibitors of cyclooxygenase (10 μM indomethacin or NS398) for 1 h. Cells were then incubated with $10^{-10}$ M DAA-I for 15 min. Values are mean±SEM from three separate experiments, each experiment was conducted in duplicate. *Significantly different from the corresponding value obtained in the absence of receptor antagonists or cylcooxygenase inhibitor (p<0.05, ANOVA, post hoc Tukey test).

Note that Losartan is a specific antagonist of the angiotensin AT1 receptor. PD123319 is a specific antagonist of the angiotensin AT2 receptor. Indomethacin is an inhibitor of both COX1 and COX2 enzymes. NS398 is a specific inhibitor of COX-2.

The inventor's conclusion is that the results show that the production of PGE2 and PGI2 was only inhibited by losartan and indomethacin confirming that des-aspartate-angiotensin I acts on the angiotensin AT1 receptor and stimulates COX1 leading to production of PGE2 and PGI2.

Figure 11:
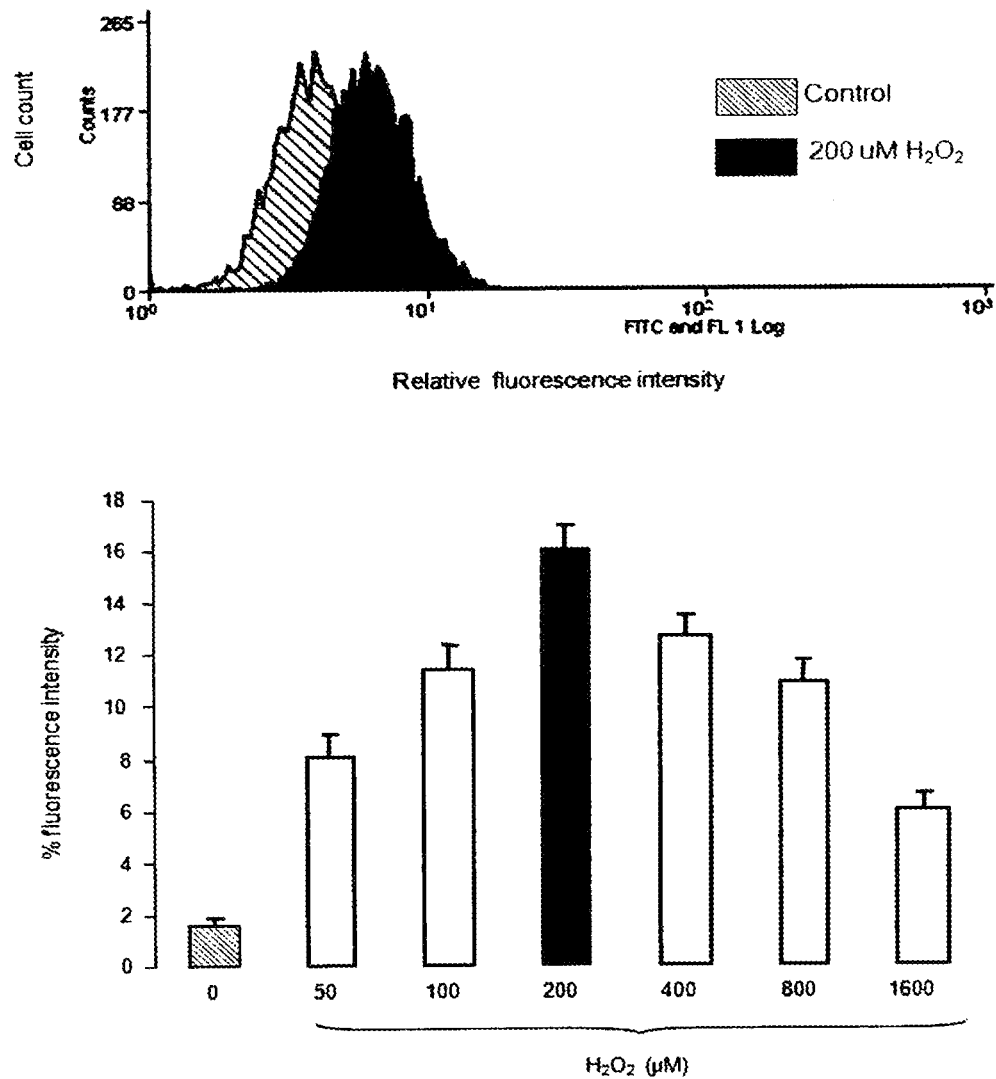

FIG. 11 shows that $H_2O_2$ induced L6 skeletal muscle cells to overexpress ICAM-1, which was quantitated by flow cytometry (upper panel). At the maximum effective dose of 200 μM, the overexpression was 8 times the basal level (lower panel).

FIG. 11 illustrates the effects of $H_2O_2$, on ICAM-1 expression in L6 skeletal muscle cells. L6 muscle cells were exposed to various concentration of $H_2O_2$ (50-1600 μM) for 4 h. The cells from each sample were then washed and treated with anti-ICAM-1 antibody and further incubated with FITC-conjugated secondary antibody. Data were collected from at least 10,000 gated viable cells by flow cytometry. Upper Panel: Flow cytometric profile of 1CAM-1 fluorescence.

Note that $H_2O_2$, concentration dependently induced overexpression of ICAM1 in L6 skeletal muscle cells. Maximum effect was observed at 200 μM, and this concentration was used in subsequent study.

Figure 12:
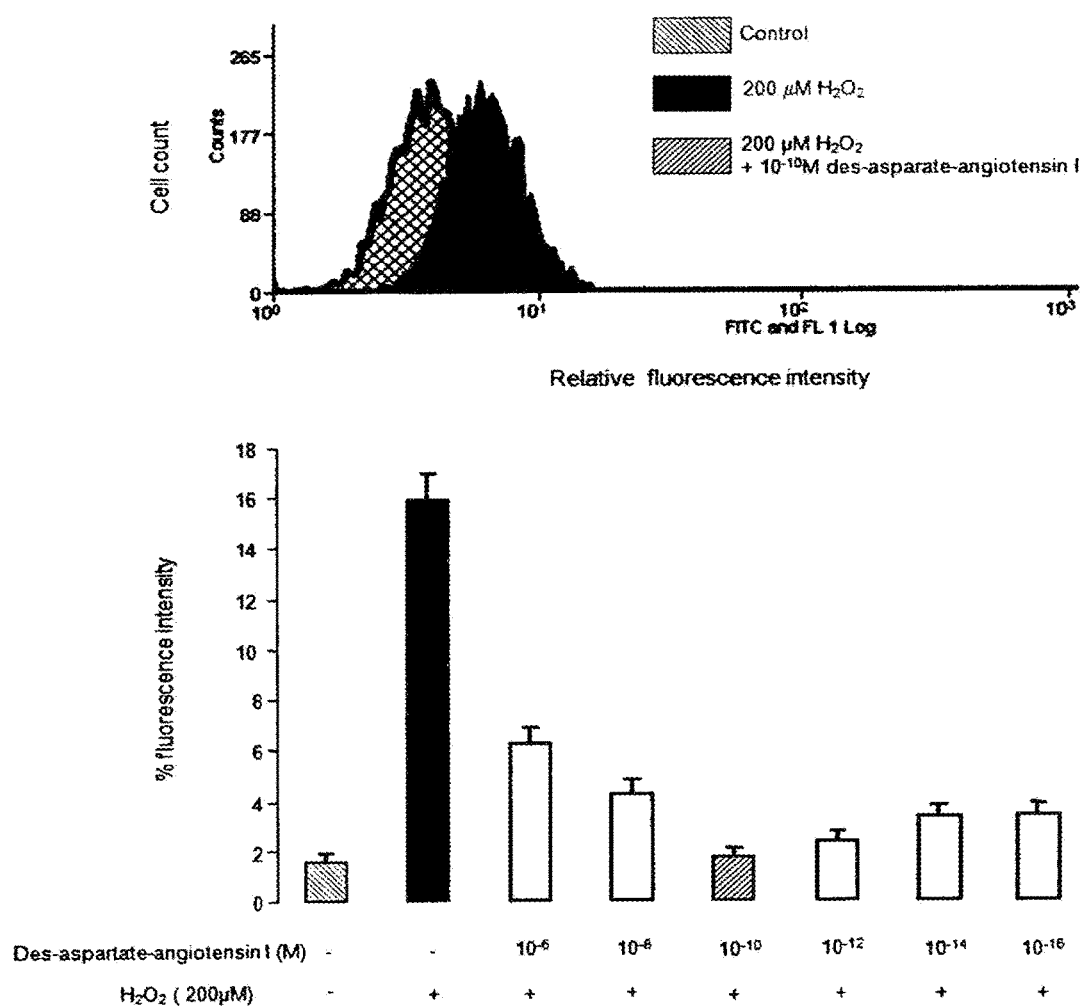

FIG. 12 shows that DAA-I attenuated the $H_2O_2$-induced overexpression of ICAM-1 in L6 skeletal muscle cells, which was quantitated by flow cytometry (upper panel). At the maximum effective dose of $10^{-10}$ M, the attenuation was 100% (lower panel).

FIG. 12 illustrates the effects of des-aspartate-angiotensin I on $H_2O_2$-induced overexpression of ICAM-1 in L6 skeletal muscle cells. L6 muscle cells were pretreated with various concentrations of des-aspartate-angiotensin I for 16 h. Following this, each sample of the muscle cells was then exposed to 200 μM of $H_2O_2$ and an additional concentration of des-aspartate-angiotensin I for a duration of 4 h. The cells from each sample were assayed for ICAM-I fluorescence as described in FIG. 11. Upper Panel: Flow cytometric profile of ICAM-1 fluorescence.

Note that DAA-1 concentration dependently attenuated the $H_2O_2$-induced overexpression of ICAM-1 in L6 skeletal muscles, with an attenuation of 100% at a concentration of $10^{-10}$ M des-aspartate-angiotensin I.

Figure 13:
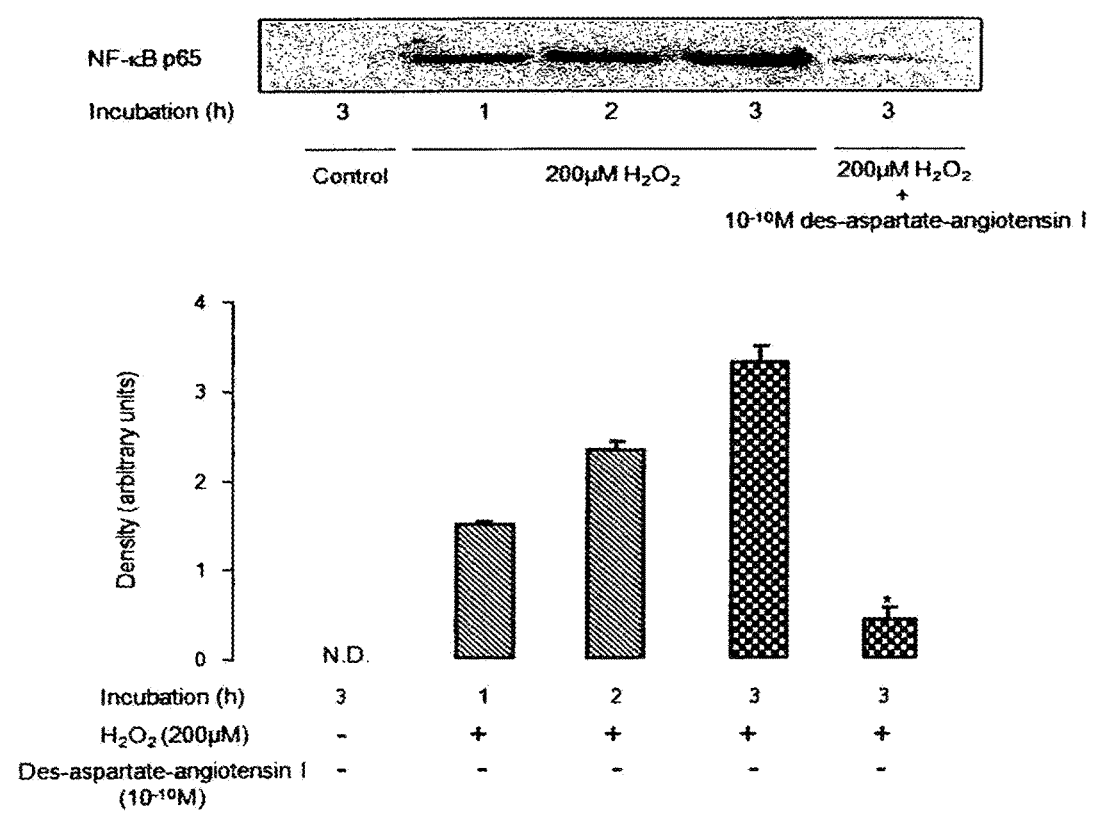

FIG. 13 shows that DAA-I attenuated that the $H_2O_2$-induced translocation of NF-κB into the nucleus of L6 skeletal muscle cells, which was quantitated by Western blotting (upper panel). At the maximum effective dose of $10^{-10}$ M, the attenuation was over 90% (lower panel).

FIG. 13 illustrates the effects of des-aspartate-angiotensin I on $H_2O_2$-induced activation and translocation of NFκB to the nucleus in L6 skeletal muscle cells. Cells were treated as described in FIG. 12. After various incubation times (1, 2, 3 hours), cells were collected and subjected to nuclear extraction. Activated NFκB that had translocated into the nucleus was determined by Western blot. Each isolated nuclear fraction (40 ug) was resolved by SDS-PAGE and probed with anti-NFκB antibody (santa-cruz, sc-109, 200× dilution) and anti-rabbit secondary antibody (santa-cruz, sc2004, 10,000× dilution). Upper panel: representative Western blot of activated NFκB proteins. Bottom panel: quantitative analysis of NFκB proteins. The vertical bars represent the SEM of samples obtained from three sets of experiments. *significantly different from the corresponding value (cells incubated with $H_2O_2$ for 3 hours).

Note that $10^{-10}$M DAA-I attenuated 90% the $H_2O_2$-induced activation and translocation of NFκB to the nucleus of L6 skeletal muscle cells.

Figure 14:
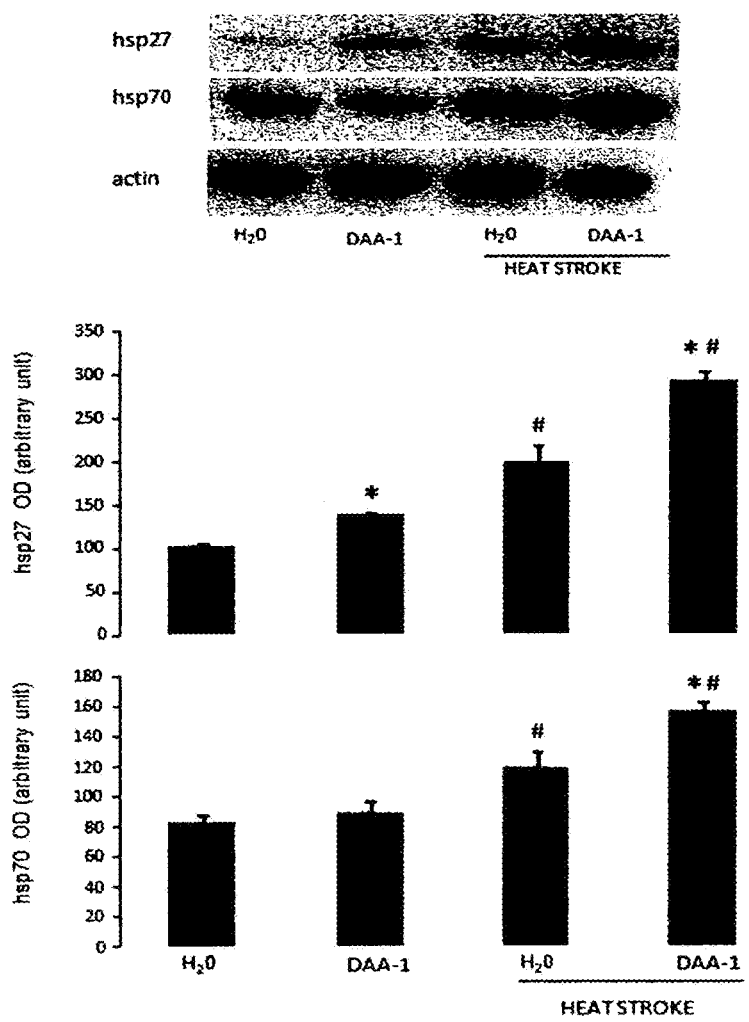

FIG. 14 shows that heat stoke increased production of hepatic heat shock proteins 27 and 70 in mice, which was quantitated by Western blotting (upper panel). Pretreatment of mice with 7.5 nmole/kg DAA-I significantly enhanced the production (lower panel). At this dose, DAA-I also protected mice from dying from heat stroke (see Table 1). The results show that DAA-I protected mice from heat stroke by enhancing the increase production of heat stoke proteins 27 and 70.

FIG. 14 illustrates the effects of DAA-I—on the expression of hepatic heat shock proteins 27 and 70 in mice exposed to heat shock Animals were orally administered 75 nmole/kg DAA-I. Control mice were administered similar volume of vehicle (0.1 ml water). Two hours after oral administration, half the number of DAA-I and water treated animals were placed in a ventilated oven set at 42° C. for a duration of 45 minutes, and the other half served as parallel non heat stroke animals. Following the heat exposure, animals were kept at room temperature for 90 minutes after which they were sacrificed and the liver of each animal was removed and homogenized. Ten μg protein were subjected to SDSPAGE and probed with hsp27. hsp70 and actin antibodies. Samples were normalized with actin expression. Each value is the mean±SEM obtained from at 7 individual animals. *Significantly different from the corresponding value of vehicle treated animal, #significantly different from the corresponding DAA-I or vehicle value in the parallel (non heat stroke) animals (p>0.05, one way ANOVA, post hoc Tukey's test).

Figure 15:
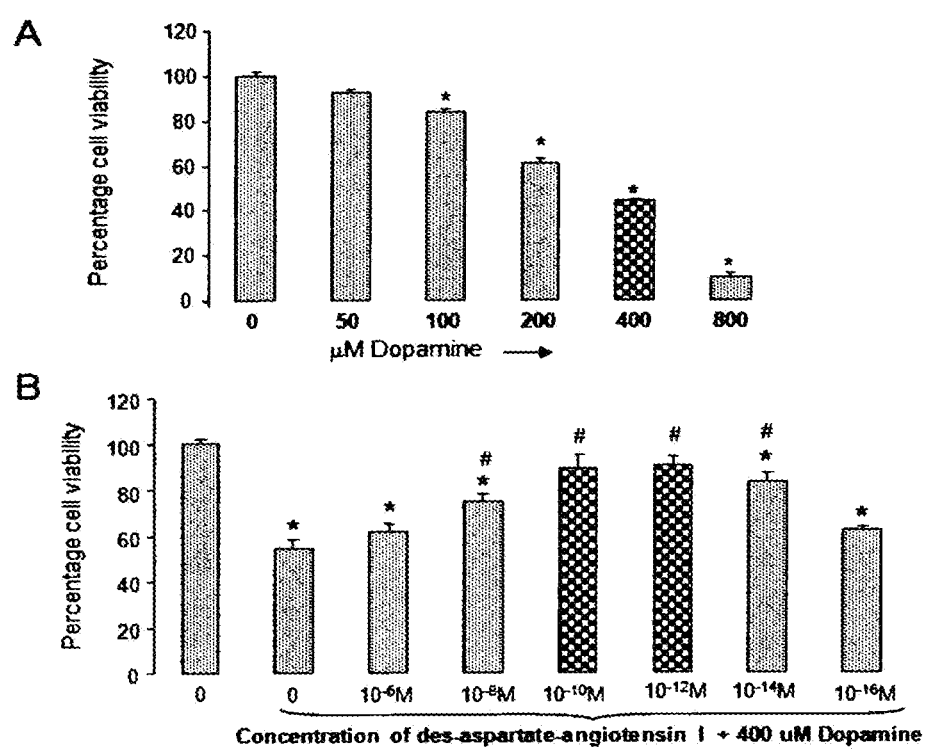

FIG. 15 shows that dopamine concentration-dependently caused death of SH-SY5Y neuroblastoma cells (upper panel). DAA-I concentration-dependently protected cell death induced by 400 μM dopamine (lower panel). At a concentration of $10^{-12}$ M, DAA-I accorded the maximum protection (over 90%).

FIG. 15 illustrates the effects of des-aspartate-angiotensin I on the survival of neuroblastoma SH-SY5Y cells cultured in high dopamine concentration. Upper panel: SH-SY5Y cells were grown in 96-well plates and treated with various concentrations of dopamine for 24 h. The cell survival after the 24 h incubation was determined by MTT assay. Dopamine concentration-dependently caused the death of SH-SY5Y with a LD50 approximating 400 μM. This concentration was used in subsequent studies. Lower panel: SH-SY5Y cells were grown in 96 well plate in the absence and presence of various concentrations of des-aspartate-angiotensin I for 24 h. Following this, the cells were treated with 400 uM dopamine and a repeat of various doses of des-aspartate-angiotensin I, and incubated for another 24 h. Cell survival after the 24 h incubation was determined by MTT assay. The vertical bars represent the SEM of samples obtained from three sets of experiments using 8 wells for each condition. *Significantly different from the non-treated control. #Significantly different from positive control. (p>0.05, one way ANOVA, Fisher's LSD).

Note that des-aspartate-angiotensin I significantly attenuated the death of SH-SY5Y neuroblastoma cells that were treated with high doses of dopamine. The maximum attenuation occurred at concentrations of $10^{-10}$ to $10^{-12}$M.

Figure 16:
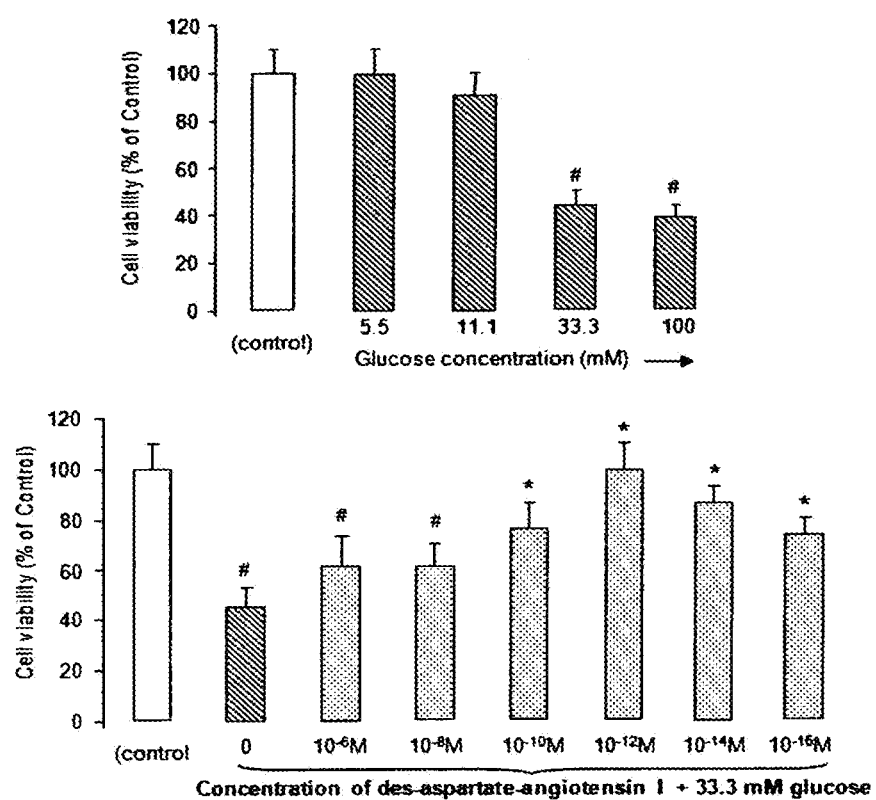

FIG. 16 shows that high glucose caused death of pancreatic beta-TC-6 cells (upper panel). DAA-I concentration-dependently protected cell death induced by 33.3 mM glucose (lower panel). At a concentration of $10^{-12}$ M, DAA-I accorded the maximum protection (over 90%).

FIG. 16 illustrates the effect of DAA-1 on the survival of pancreatic beta-TC-6 cells cultured in high glucose concentration. Upper panel: Beta-TC-cells were cultured in 96 well plate in the presence of various concentrations of glucose that were added to the DMEM culture medium. The basal glucose concentration in the DMEM culture medium was 25 mM. Their survival was determined by MTT assay after 4 days of incubation. Glucose concentration-dependently caused the death of the beta-TC-6 cells with a LD50 approximating 33.3 mM. This concentration was used in subsequent studies. Lower panel: Beta-TC-cells were cultured in 96-well plate in the presence of additional 33.3 mM glucose, and in the absence and presence of various concentrations of DAA-I. Their survival was similarly determined after 4 days of incubation. The vertical bars represent the SEM of samples obtained from three sets of experiments using 8 wells for each condition. *Significantly different from control. #Significantly different from reading obtained in the absence of DAA-1 (p>0.05, ANOVA followed by post hoc Tukey's test).

Note that des-aspartate-angiotensin I significantly attenuated high glucose-induced death of beta-TC-6 cells. The maximum attenuation occurred at a concentration of $10^{-12}$M des-aspartate-angiotensin I.

Figure 17:
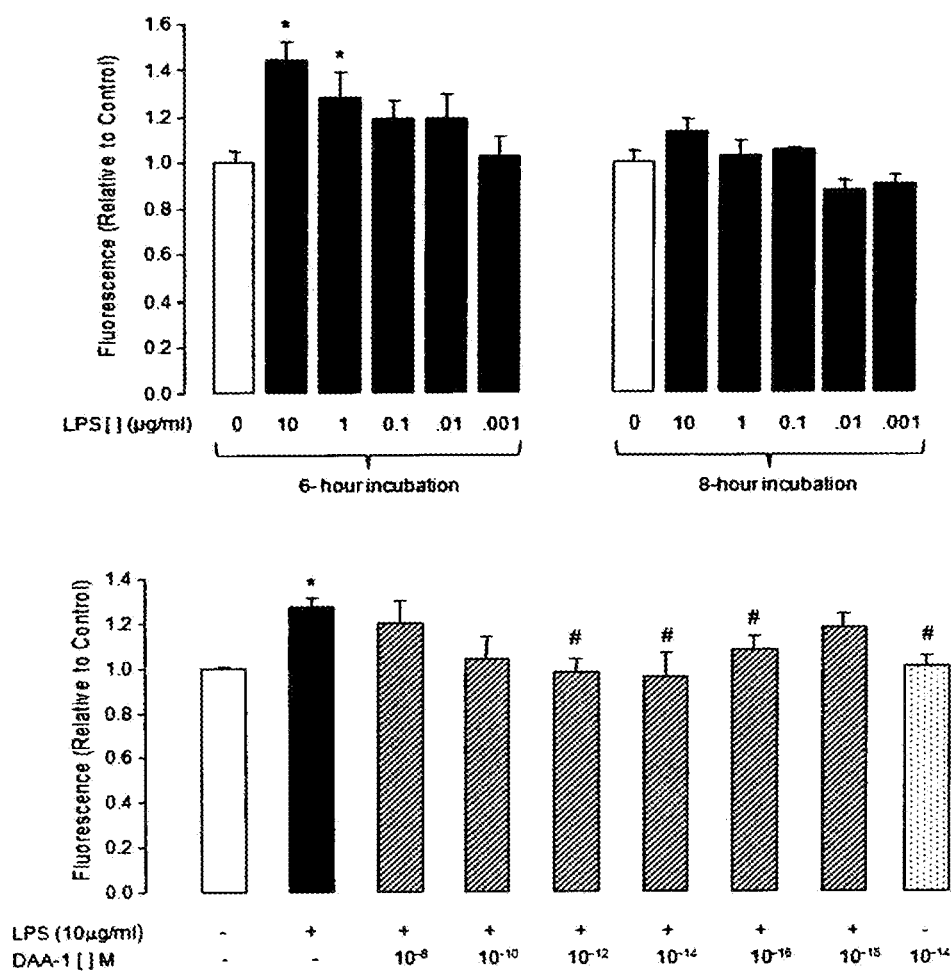

FIG. 17 shows that LPS increased production of superoxide production in A549 cells (upper panel). DAA-I concentration-dependently inhibited the production (lower panel). At a concentration of $10^{-12}$M, the inhibition was complete.

FIG. 17 illustrates the effects of DAA-I on LPS-induced superoxide production in A549 cells. Upper panel: Cells were challenged with serial dilutions of LPS (10-0.001 μg/ml) and the production of superoxide was assayed by DHE fluorescence at 6 and 8 hours post infection. Lower panel: A549 cells were challenged with 10 μg/ml LPS and simultaneously treated with varying doses of DAA-I for 6 hours. After the 6 or 8-hour incubation period at 37° C. and 5% $CO_2$, culture media were aspirated from wells and cells incubated with 5 μM DHE for 30 minutes. Error bars represent ±SEM of 3 experiments. *Significantly different from the negative control (untreated cells, hollow histogram, #significantly different from the positive control (LPS-treated cells, solid histogram), (1-way ANOVA, post-hoc Tukey HSD). Note that $10^{-14}$M DAA-1 by itself had no effect on the basal level of superoxide in cultured A549 cells.

Figure 18:
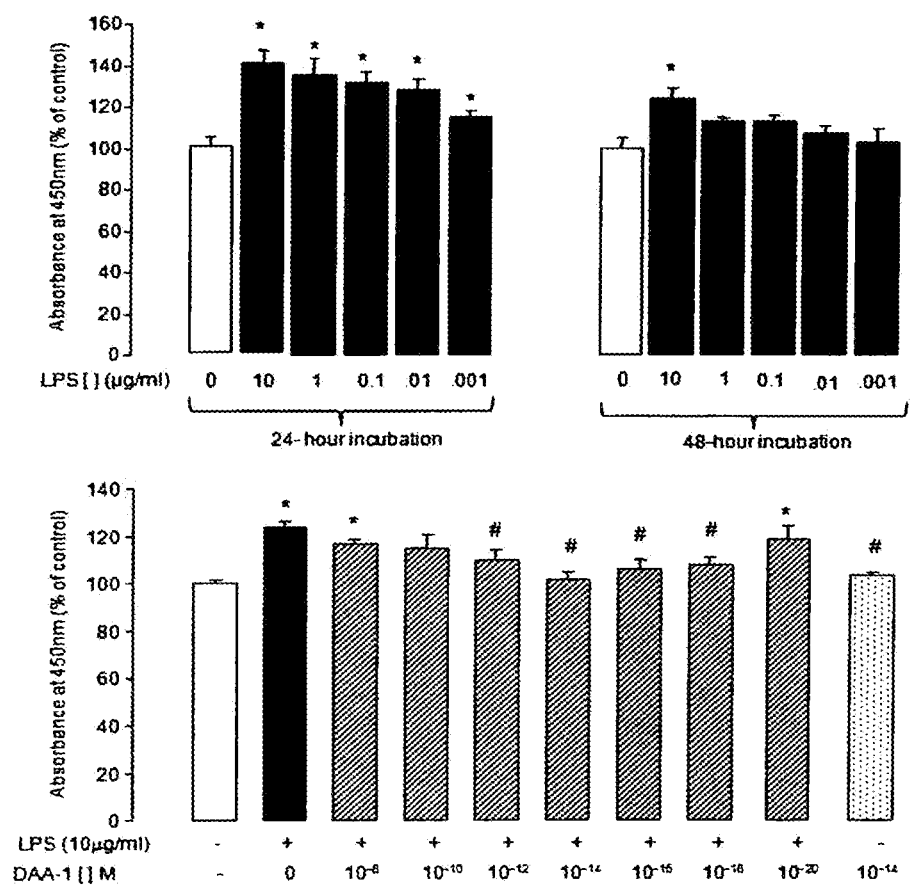

FIG. 18 shows that LPS increased production of E-selectin in A549 cells (upper panel). DAA-I concentration-dependently inhibited the production (lower panel). At a concentration of $10^{-12}$ M, the inhibition was complete.

FIG. 18 illustrates the effects of DAA-I on E-selectin expression in LPS-challenged A549 cells. Upper panel: A549 cells were challenged with serial dilutions of LPS (10-0.001 μg/ml) and assayed for E-selectin production by ELISA at 24 and 48 hours post-infection. Lower panel: A549 cells were challenged with 10 μg/ml LPS and simultaneously treated with varying doses of DAA-I for 24 hours. After the 24 or 48-hour incubation period at 37° C. and 5% $CO_2$, culture media were aspirated from wells and cells were fixed by incubation with 100% ice-cold ethanol for 10 min. E-selectin expression on cell surface was assayed by ELISA. Absorbance at 450 nm was normalized against the negative controls (cells only). Error bars represent ±SEM of 3 experiments. *Significantly different from the negative control (untreated cells, hollow histogram), #Significantly different from the positive control (LPS-treated cells, solid histogram), (1-way ANOVA, post-hoc Tukey HSD). Note that $10^{-14}$M DAA-1 by itself had no effect on the basal level of superoxide in cultured A549 cells.

Figure 19:
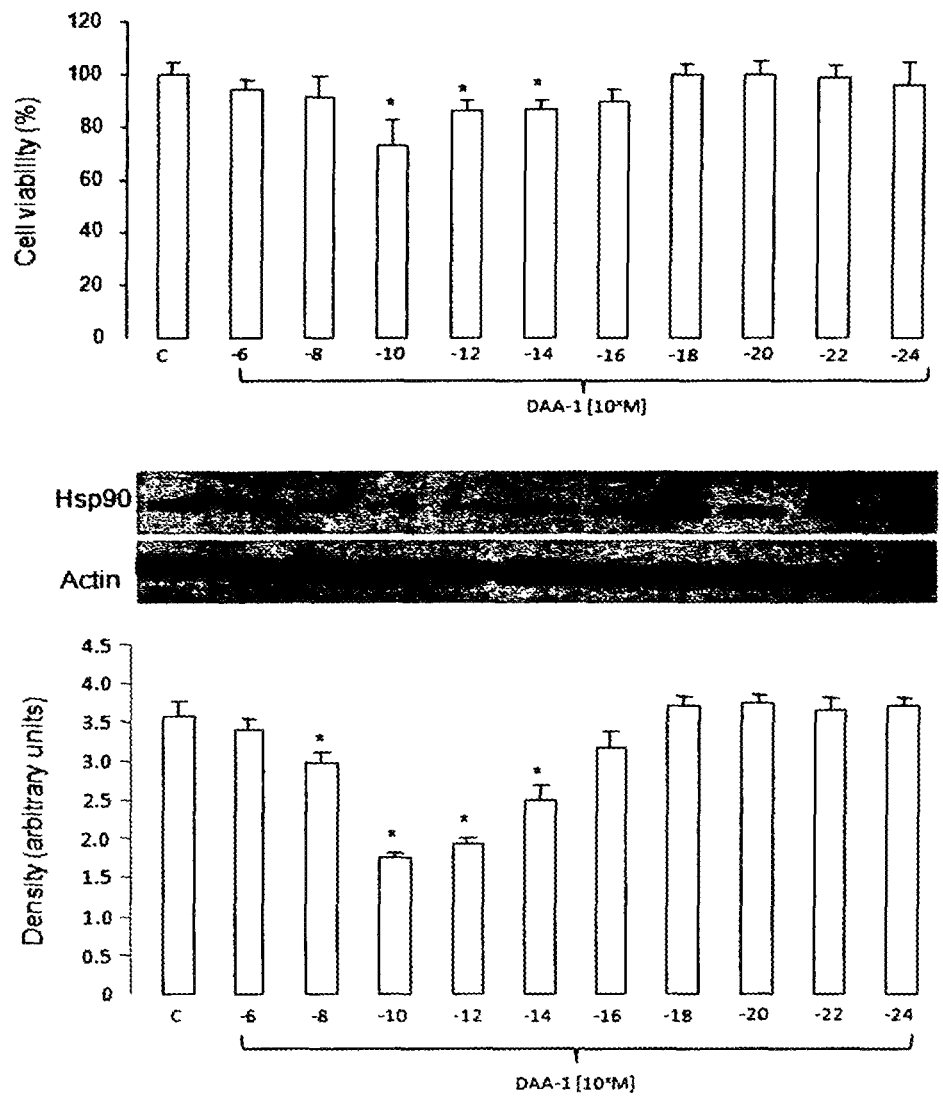

FIG. 19 shows that DAA-I concentration-dependently inhibited viability of cultured B16-F10 melanoma cells (upper panel), and production of heat shock protein 90 in the same cells (lower histograms). The maximum effect occurred at $10^{-10}$ M DAA-I.

FIG. 19 illustrates the effects of des-aspartate-angiotensin I on cell viability and Hsp90 content in melanoma cells. Upper histograms: Cell viability in different concentrations of des-aspartate-angiotensin I. Lower histograms: Hsp90 content in cells grown in different concentrations of des-aspartate-angiotensin I.

DETAILED DESCRIPTION OF THE INVENTION

Definition of Derivatives of Des-Aspartate-Angiotensin I

First Definition:

Derivatives of des-aspartate-angiotensin I are defined as peptides containing nine or less aminoacids in which arginine and histidine constitute the first and fifth aminoacid, respectively, of each sequence or only arginine is present as the original first aminoacid, and only histidine is present as the original fifth aminoacid of each sequence. This definition was based on an earlier study showing that the critical aminoacids of des-aspartate-angiotensin I that are responsible for its activity are arginine and histidine placed in position of 1 and 5 of the peptide sequence, respectively (Chen et al., Regul. Pept., 106:39-46 (2002)) and that angiotensin IV, a secondary metabolite of des-aspartate-angiotensin I that lacks arginine as the first aminoacid is also effective in combating cardiac hypertrophy and restenosis (PCT No. WO 2006/078223 A1).

Second Definition:

Derivatives of des-aspartate-angiotensin I are also defined as peptide fragments that are its metabolites. These include peptide fragments such as, but not restricted to, Tyr-Ile-His-Pro-Phe (SEQ ID NO: 1), Ile-His-Pro-Phe (SEQ ID No: 2), Val-Tyr. These three peptides have been shown to exert hypoglycemic action in C57BL/6J mice (see Example 10).

Example 1

Source of Materials

Des-aspartate-angiotensin I was purchased from Peptisyntha (Belgium). Tyr-Ile-His-Pro-Phe (SEQ ID NO: 1), Ile-His-Pro-Phe (SEQ ID NO: 2), and Val-Tyr were purchased from Bachem (Switzerland). Des-aspartate-angiotensin I and the three angiotensin fragments can be prepared by techniques well known in the art. 2-chloroethyl ethyl sulfide (known as half sulfur mustard) was purchased from Sigma-Aldrich (St. Louis, Mo.). Virus and cell lines were purchased from ATCC (Manassas, Va.). All antibodies were purchased from Santa Cruz Biotechnology (Santa Cruz, Calif.). Prostaglandin assay kits were purchased from Cayman Chemical Company (Ann Arbor, Mich.). HUVEC was purchased from VEC Technologies (Rensselaer, N.Y.). Balb/c and C57BL/6J mice were obtained from the Animal Center, National University of Singapore.

Example 2

Development of a Mouse Model of Lung Inflammation with Half Sulfur Mustard

Half sulfur mustard is a vesicant, and when inoculated into the lungs of mice causes intense lung inflammation and death. By adjusting the lethal dose of the half sulfur mustard, animals could be made to survive and serve as model of lung inflammation for the study of the anti-inflammation actions of des-aspartate-angiotensin I. The protocols to be described in Examples 3 to 7 are part of a research project that studied counter measures and antidotes against vesicant compounds that could be used as chemical weapons by terrorists. Since the filing of the present patent, the protocols and the findings of this research have been accepted for publication (Ng et al., J. Appl. Toxicol. (Epub ahead of print, 9 Nov. 2010)).

Nine to 10 weeks old Balb/c mice were randomly allotted into 5 groups of 7 mice. The mice were anaesthetized with avertin and intranasally inoculated with various doses of half sulfur mustard dissolved in 25 µL 50% ethanol. Animals in the control group were inoculated with vehicle. The survival of the mice was monitored for 21 days. Half sulfur mustard dose-dependently increased the mortality of the animals. The study was repeated. The dose of 0.28 mg/kg in which 65% of the animals had died by Day 21 (LD65) was used to study the anti-inflammatory action of des-aspartate-angiotensin I.

Example 3

Monitoring and Treatment (with Orally-Administered Des-Aspartate-Angiotensin I) of Half Sulfur Mustard-Inoculated Balb/c Mice Mice were randomly allotted into 6 groups of 10 mice. The animals were intranasally inoculated with LD65 half sulfur mustard as described above. The animals were then orally administered (by gavage) various dose of des-aspartate-angiotensin I in 0.1 ml water daily for 14 days. Animals in the control group were administered vehicle. The survival of the mice was monitored for 21 days. The study was repeated twice. Des-aspartate-angiotensin I dose-dependently attenuated the mortality of half sulfur mustard-inoculated mice. The dose of 75 nmole/kg exerted maximum attenuation. At this dose 20 out of 30 mice survived as compared with 10 out of 30 mice in the control group. This dose was used in subsequent studies on the anti-inflammatory actions of des-aspartate-angiotensin I in pulmonary tissues of half sulfur mustard-inoculated mice. The protocols of water or des-aspartate-angiotensin I administration (treatment) were also adopted (in Examples 4-7).

Example 4

Figure 1:
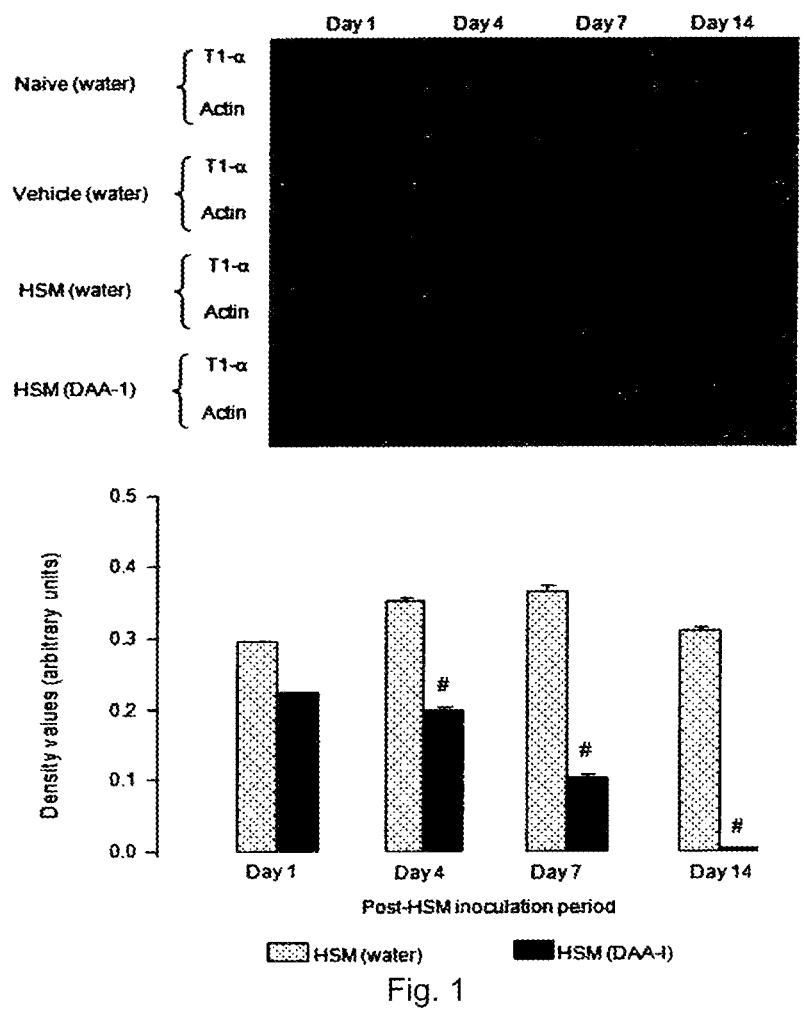
FIG. 1 shows that HSM damaged lung alveoli in mice. Damaged type 1 alveolar cells released T1α protein, which was quantitated by Western blotting (upper panel). DAA-I, given at a dose of 75 nmole/kg/day, significantly attenuated the release of T1α protein and complete attenuation was seen at 14 day of treatment (lower panel).

Effect of Orally-Administered Des-Aspartate-Angiotensin I on the Presence of T1α Protein in Bronchoalveolar Lavage Fluid (BALF) of Mice Inoculated with Half Sulfur Mustard Type 1 alveolar cells produce T1α protein (which is specific to the cells). The damaging effects of half sulfur mustard on the alveoli could be measured by assaying the level of T1α protein in BALF. BALF is obtained by flashing the lungs of anaesthetized mice with 0.5 ml of buffered saline. The results of the study are summarized in FIG. 1, which shows that des-aspartate-angiotensin I significantly attenuated the level of T1α protein in BALF of mice inoculated with half sulfur mustard, confirming that des-aspartate-angiotensin I blocks the damaging actions of half sulfur mustard.

Example 5

Figure 2:
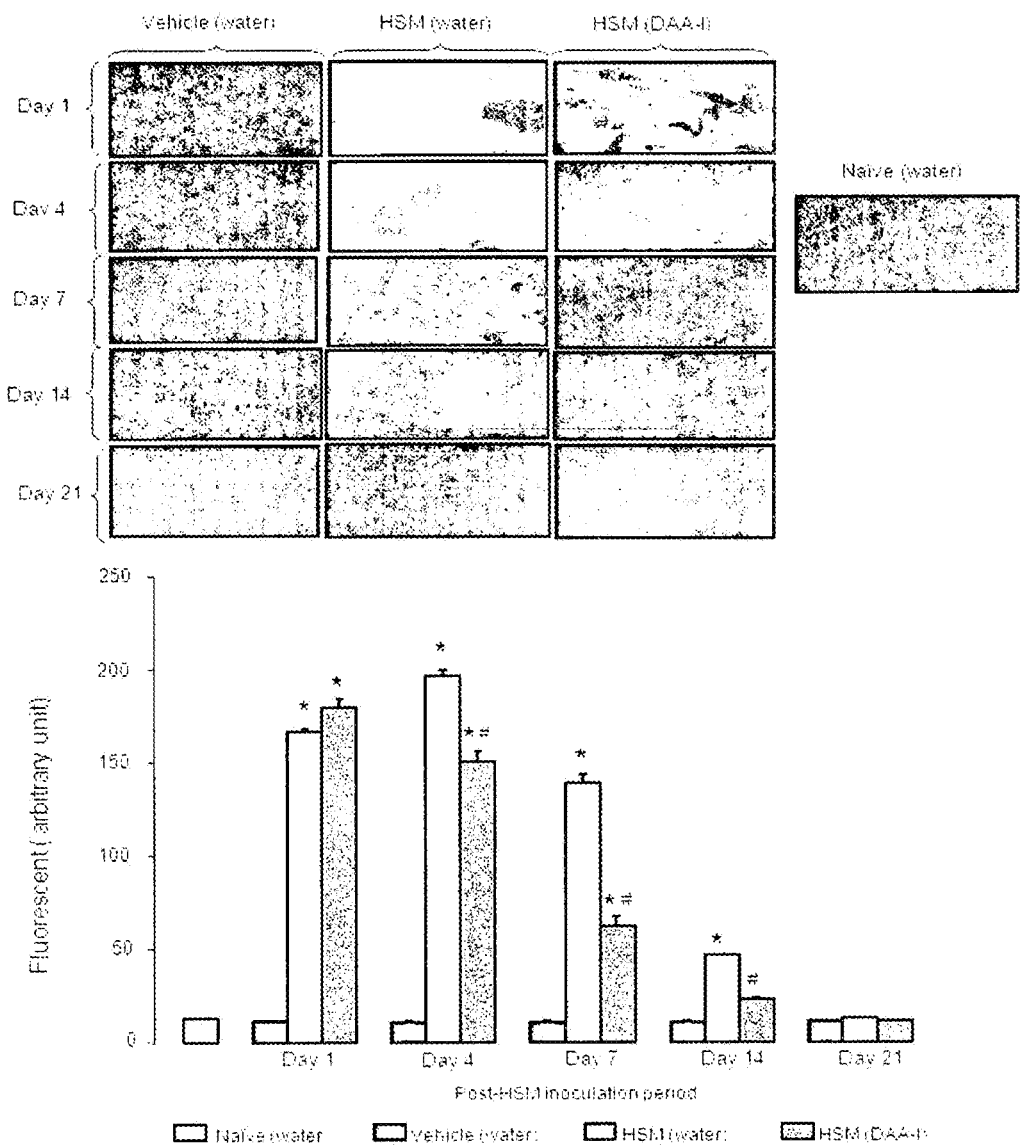
FIG. 2 shows that HSM caused an increase in superoxide production in the lung of mice, which was quantitated colormetrically (upper panel). Excessive superoxide cause significant damage to cell structures. DAA-I treatment (75 nmole/kg/day) significantly attenuated the production of superoxide from day 4 to end of treatment at day 14 (lower panel).
Figure 3:
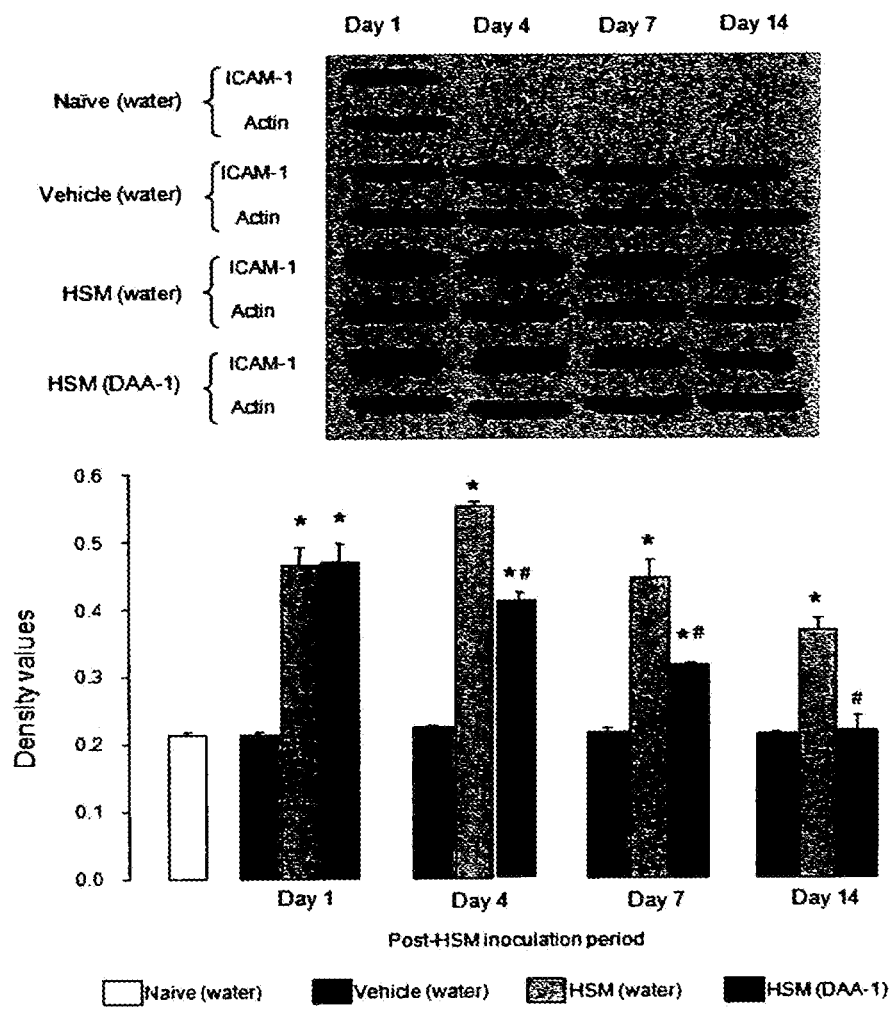
FIG. 3 shows that HSM caused an increase in ICAM-1 production in the lung of mice, which was quantitated by Western blotting (upper panel). ICAM-1 is produced by injured lung endothelial cells. It recruits leucocytes to site of injury resulting in inflammation. DAA-I treatment (75 nmole/kg/day) significantly attenuated the production of ICAM-1 from day 4 to end of treatment at day 14 (lower panel).
Figure 4:
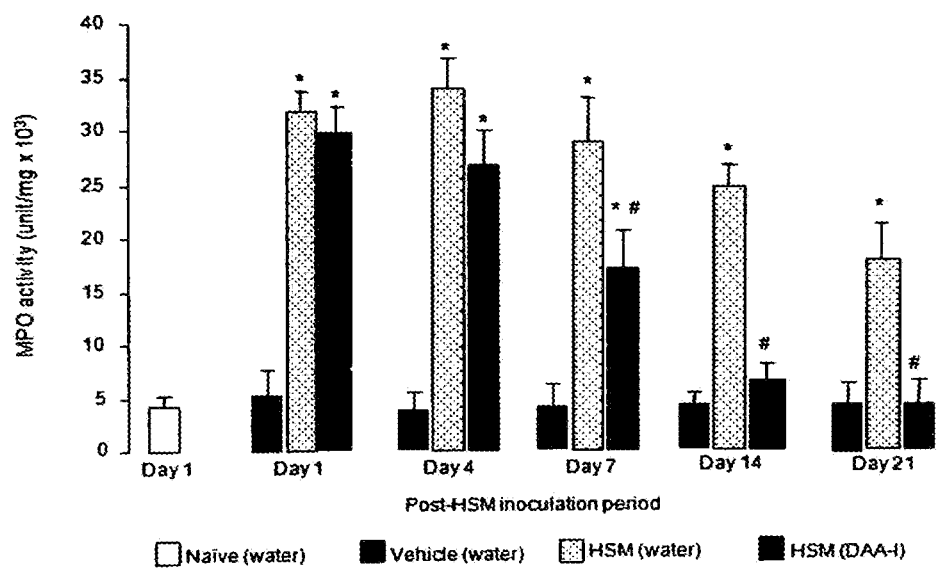
FIG. 4 shows that HSM caused an increase in MPO level in the lung of mice. MPO is a specific enzyme of neutrophils. Increased level of MPO in the lung indicates increased neutrophil infiltration and inflammation. DAA-I treatment (75 nmole/kg/day) significantly attenuated the level of lung MPO and in this way attenuated the inflammation caused by HSM.
Figure 5:
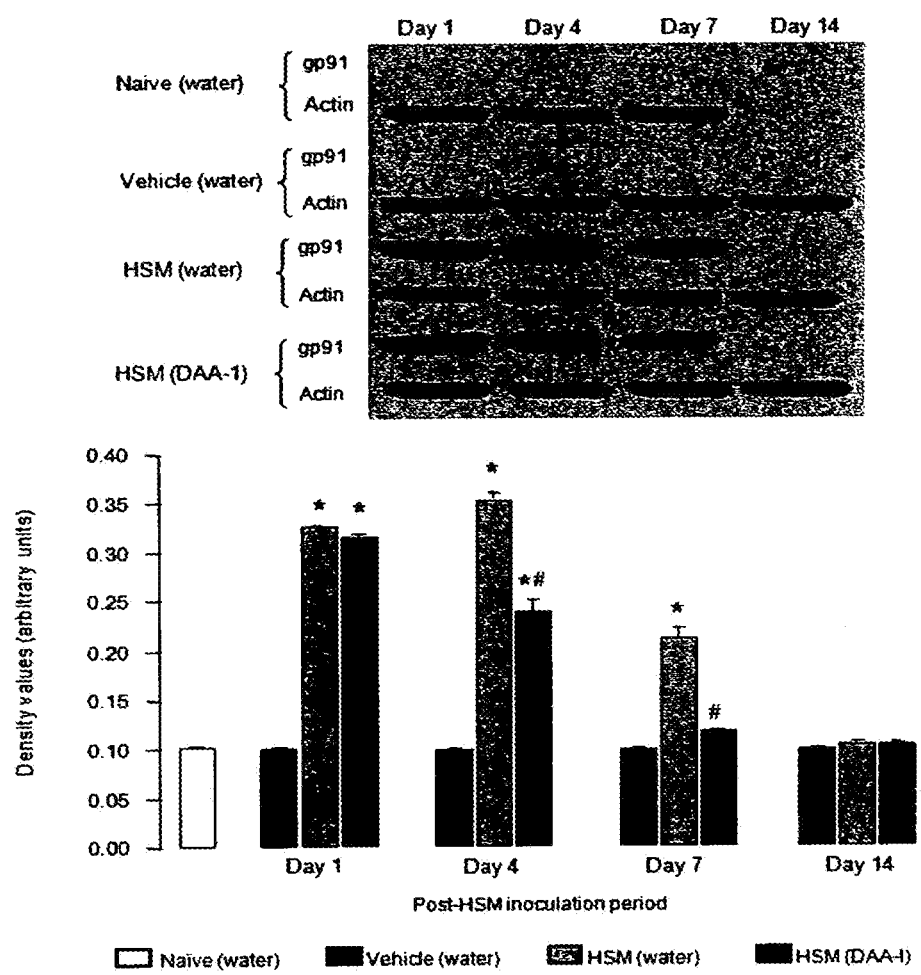
FIG. 5 shows that HSM caused an increase in gp91-phox protein in the lung of mice, which was quantitated by Western blotting (upper panel). gp91-phox protein is an integral component of NADPH oxidase, the enzyme that generated superoxide. DAA-I treatment (75 nmole/kg/day) significantly attenuated the increase in lung gp81-phox protein (lower panel).

Effect of Orally-Administered Des-Aspartate-Angiotensin I on the Overproduction of Superoxide, Intercellular Adhesion Molecule-1 (ICAM-1), and Infiltration of Neutrophil in Lungs of Mice Inoculated with Half Sulfur Mustard At site of cellular damage, pro-inflammatory mediators, e.g. superoxide and cytokines, are released from damaged or injured cells. These inflammatory mediators induced formation of adhesion molecules, e.g. ICAM-1 and selectins, which attract leucocytes, e.g. neutrophils and macrophages, to the site of cellular damage. The leucocytes extravasate and produce cytokines of their own and initiate the process of inflammation. FIGS. 2-4 show that des-aspartate-angiotensin I attenuated these three early processes of inflammation, i.e. the increase in pulmonary production of superoxide and ICAM-1, and infiltration of neutrophils into the lung of mice. The infiltration of neutrophils was measured by assaying myloperoxidase (MPO), a specific enzyme produced by neutrophils. The source of superoxide is NADPH oxidase (Bedard and Krause, Physiol. Rev., 87:245-313 (2008)), and FIG. 5 shows that des-aspartate-angiotensin I attenuates the upregulated NADPH oxidase.

Example 6

Involvement of PGE2 and PGI2 in the Anti-Inflammatory Actions of Des-Aspartate-Angiotensin I (in Lungs of Mice Inoculated with Half Sulfur Mustard)

Figure 6:
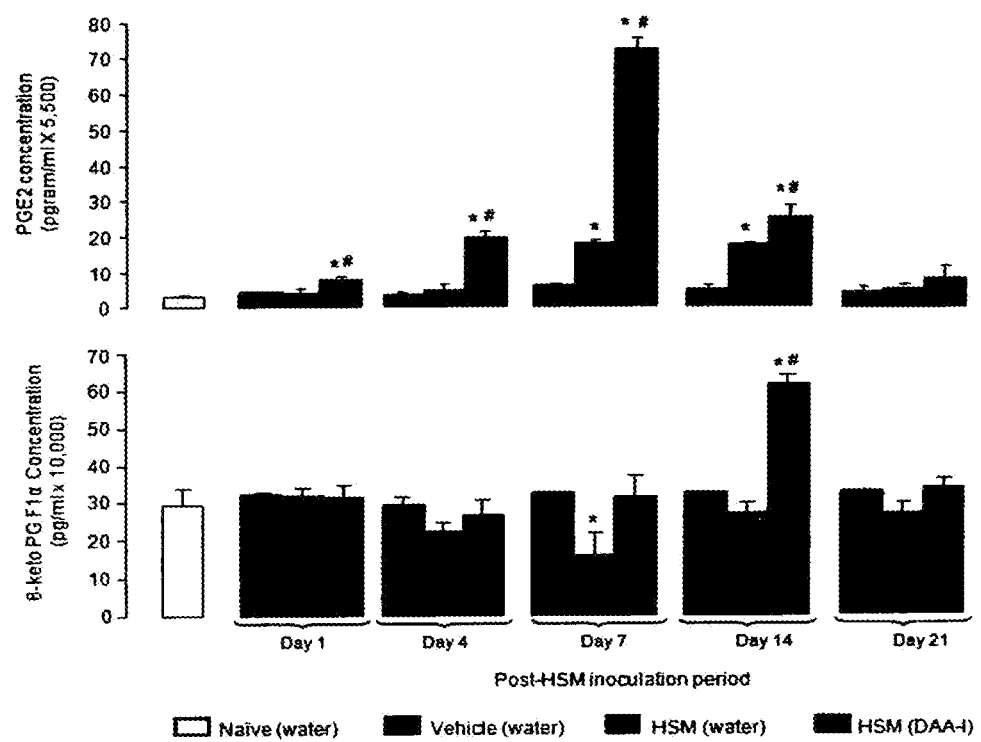
FIG. 6 shows that HSM caused a temporal increase in PGE2 (upper panel) and a decrease in PGI2 (lower panel) in the lung of mice. DAA-I treatment (75 nmole/kg/day) significantly enhanced the increase in PGE2 and attenuated the decrease in PGI2. These findings show that PGE2 and PGI2 are involved in the action of DAA-I. (Ng et al., J. Appl. Toxicol. (Epub ahead of print, 9 Nov. 2010)).

FIG. 6 shows the involvement of PGE2 and PGI2 in the anti-inflammatory actions of des-aspartate-angiotensin I in the half sulfur mustard inoculated mouse lung. Half sulfur mustard induced an elevation of pulmonary PGE2 in the period between 7 and 14 days post exposure. Des-aspartate-angiotensin I treatment exaggerated the onset and magnitude of this elevation. Significant increase of the prostaglandin was observed on Day 1, and peak level on Day 7 post exposure. PGI2, measured as its stable metabolite 6-keto PGF1α, showed an opposite trend. Its concentration decreased following HSM exposure and maximum decrease occurred at Day 7 post exposure. Des-aspartate-angiotensin I treatment attenuated the decreasing trend, and a marked increase in the prostaglandin was seen at Day 14 post exposure.

Example 7

Des-Aspartate-Angiotensin I Exerts its Anti-Inflammation Actions Via the Angiotensin AT1 Receptor (in Mice Inoculated with Half Sulfur Mustard)

Figure 7:
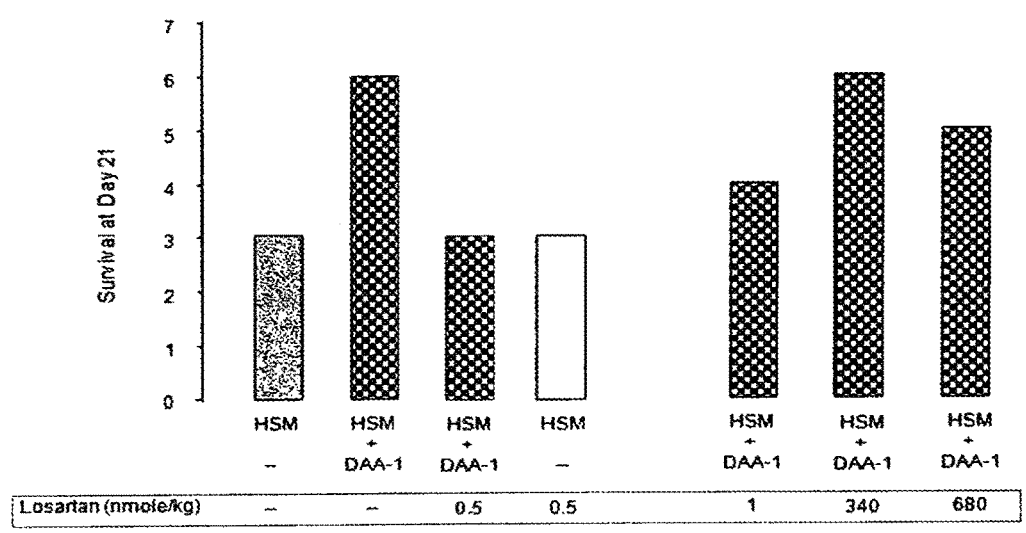
FIG. 7 shows that the protective action of DAA-I against HSM intoxication was blocked by losartan, an angiotensin AT1 receptor blocker. At a dose of 0.5 nmole/kg, losartan by itself had no effect on the survival of HSM-intoxicated mice. However, this dose when given together with DAA-I completely blocked the protective action of DAA-I showing the angiotensin AT1 receptor mediate the protective action of DAA-I.

The angiotensin AT1 receptor is characterized by its susceptibility to blockade by losartan (de Gasparo et al., Pharmacol. Rev., 52:415-472 (2000)). Hence, biological responses mediated by the angiotensin AT1 receptor are blocked by losartan. To show that the actions of des-aspartate-angiotensin I are mediated by the angiotensin AT1 receptor, its anti-mortality (which is the resultant of its anti-inflammation actions) was subjected to blockade by losartan. FIG. 7 shows that losartan completely attenuated the anti-mortality action of des-aspartate-angiotensin I confirming that the nonapeptide acts on the angiotensin AT1 receptor.

Example 8

Des-Aspartate-Angiotensin I Specifically Releases PGE2 and PGI2 Via its Action on the Angiotensin AT1 Receptor The endothelium is intimately involved in inflammation (Pober and Sessa, Nat. Rev. Immunol, 7:803-815 (2007)), and human umbilical vein endothelial cells (HUVEC) are extensively used to study its role in inflammation (Boyle et al., Circulation 98:(19 Suppl):II282-II288 (1998); Ferrante et al., Cir. Res., 99:34-41 (2006)). FIG. 8 shows that des-aspartate-angiotensin I specifically releases PGE2 and PGI2 from HUVEC at the sub nanomolar concentration of $10^{-10}$ M. At 100,000 times this concentration ($10^{-5}$ M), its actions become non specific and mimic those produced by $10^{-7}$ M angiotensin II. FIG. 9 shows des-aspartate-angiotensin I had no effect on the production of PGF2α and thromboxane A2. In similar studies carried out with a concentration range of $10^{-12}$ to $10^{-5}$ M, des-aspartate-angiotensin I exerts non specific action at a concentration of $10^{-6}$ M. However in terms of clinical uses, a drug is never administered at concentrations 10,000 times higher than its effective concentration. FIG. 10 shows that the action of des-aspartate-angiotensin I is mediated by the angiotensin AT1 receptor, and COX1 is the enzyme involved in the production of PGE2 and PGI2.

Example 9

Effect of Orally-Administered Des-Aspartate-Angiotensin I on Other Inflammatory Pathologies and Diseases The ability of des-aspartate-angiotensin I to exert anti-inflammatory actions in inflammatory pathologies and related disease was studied in the following in vitro and in vivo biological systems:

a. Skeletal Muscle Damage

Unaccustomed and excessive strenuous exercise causes skeletal muscle damage. Both in vivo and in vitro studies indicate that reactive oxygen species (ROS) play a critical role in the damage (Sachdev and Davis, Free Radic. Biol. Med., 44:215-223 (2008); Wataru et al., Free Radic. Biol. Med., 37:480-487 (2004); Sen et al., Biochem. Biophys. Res. Commun., 237:645-649 (1997); Maruhashi et al., J. Physiol. Sci., 57:211-216 (2007); Kerkweg et al., Shock 27:552-558)). Oxidative stress, structural muscle damage, and muscle inflammation (resulting from the exercise) generate excess ROS that overwhelm cellular antioxidant defenses and cause tissue damage. The effect of des-aspartate-angiotensin I in overcoming $H_2O_2$ (an important ROS)-induced ICAM-1 formation in L6 skeletal muscle cells was studied. FIGS. 11 and 12 show that L6 skeletal muscle cells overexpressed an 8-fold increase in ICAM-1 when incubated with 200 μM $H_2O_2$, and des-aspartate-angiotensin I concentration-dependently attenuated the $H_2O_2$-induced overexpression of ICAM-1 with a remarkable 100% attenuation at a concentration of $10^{-10}$ M. In muscle damage, ROS like $H_2O_2$ activates NF-κB and causes its translocation into the nucleus. Following this, NF-κB stimulates the transcription of its target genes resulting in the synthesis of proinflammatory proteins including ICAM-1, which trigger the inflammatory cascade (Wataru et al., Free Radic. Biol. Med., 37:480-487 (2004); Sen et al., Biochem. Biophys. Res. Commun., 237:645-649 (1997)). FIG. 13 shows that, under similar conditions in which des-aspartate-angiotensin I attenuated ICAM-1 overexpression, the activation and translocation of NF-κB to the nucleus was >90% attenuated by $10^{-10}$ M des-aspartate-angiotensin I.

b. Heat Stroke

Heat stroke is a life-threatening illness caused by an extreme increase in core body temperature as a result of exposure to high ambient temperature or strenuous exercise. Despite the availability of intensive medical intervention, heat stroke is often fatal and effective therapy is lacking (Bouchama and Knochel, N. Engl. J. Med., 346:1978-1988 (2002)). The reasons could be due to the systemic inflammatory responses to heat stroke, which are in many ways similar to those of sepsis that lead to multi-organ failure. Heat stroke is often fatal and our study was devised to test the effect of DAA-I on the survival of mice exposed to heat stroke. The study was based on the method described by Mota et al. (Crit. Care Med. 36:526-534 (2008)). Ten 8 to 9 weeks old male C57/BL/6J mice were randomly group into 2 groups of 5 animals. One group was orally administered (by gavage) 7.5 nmole/kg des-aspartate-angiotensin I and the other group (control group) was similarly administered vehicle. Two hours after des-aspartate-angiotensin I administration, the animals were placed in a cage that was preheated to 42° C. in a ventilated oven (Labnet Model 211DS). The animals were continuously exposed to 42° C. for 45 min. The number of animals that survived the first 24 hours following the 45 min heat exposure was recorded. Two such experiments were performed. Table 1 shows that des-aspartate-angiotensin I increased the survival of mice subjected to heat stroke.

TABLE 1

Effect of des-aspartate-angiotensin I on survival of mice subjected to heatstroke

| Dose of Des-aspartate-angiotensin I | Survival (Number out of 5 animals) | |
|---|---|---|
| | Female Mice | Male Mice |
| 0 (vehicle) | 2 | 1 |
| 7.5 nmole/kg | 4 | 4 |
| 0 (vehicle) | 3 | 0 |
| 7.5 nmole/kg | 5 | 4 |

FIG. 14 shows that heat stroke increased production of hepatic heat shock protein 27 and 70 in C57BL/6J mice, which is in concordance with similar findings of Mota et al. (Crit. Care Med. 36:526-534 (2008)). Des-aspartate-angiotensin enhanced the production of heat shock protein 27 and 70, and the enhancement is a likely mechanism of its protective actions action. The dose of 7.5 nmole/kg was determined to be an effective dose in preliminary dose-response experiments.

c. ICAM-1 Production in HUVEC

Pro-inflammatory cytokines increase ICAM-1 expression in a variety of cells, and this occurs in the early stages of inflammation (Hubbard and Rothlein, Free Radic. Biol. Med., 28:1379-1386 (2000)). TNF-α is a major pro-inflammatory cytokine and has been used to stimulate ICAM-1 production in HUVEC for study of anti-inflammatory agents (Zhou et al., Eur. J. Pharmacol., 513:1-8 (2005); Gutierrez et al., Atherosclerosis 190:90-99 (2007)). Similar protocols were used to study the anti-inflammatory actions of des-aspartate-angiotensin I. HUVEC were exposed to 4 ng/ml TNF-α and various concentrations of des-aspartate-angiotensin I for 6 hours. The cells from each sample were then washed and treated with anti-ICAM-1 antibody and further incubated with FITC-conjugated secondary antibody. ICAM-1 level in each sample was determined by flow cytometry as described in FIG. 12. Table 2 shows that des-aspartate-angiotensin I attenuated the TNF-α-induced upregulation of ICAM-1 production in HUVEC. Maximum attenuation occurred at a concentration of $10^{-10}$ M.

TABLE 2

Effect of des-aspartate-angiotensin I on TNF-α-induced production of ICAM-1 in HUVEC

| Doses of drugs | % of Fluorescence |
|---|---|
| Vehicle (PBS) | 3 ± 0.13 |
| 4 ng/ml TNF-α | #12 ± 1.6 |
| 4 ng/ml TNF-α + $10^{-8}$ M des-aspartate angiotensin I | #*6 ± 1.1 |
| 4 ng/ml TNF-α + $10^{-10}$ M des-aspartate angiotensin I | *3 ± 0.35 |
| 4 ng/ml TNF-α + $10^{-12}$ M des-aspartate angiotensin I | #*5 ± 0.43 |

Significantly different from the vehicle value
*Significantly different from the 4 ng/ml TNF-α value d. Dopamine-Induced Neuroblastoma SH-SY5Y Cell Death Enhanced oxidative stress has been implicated in the genesis of Parkinson's disease, and dopamine is a major cause of the oxidative stress (Hasting et al., Proc. Natl. Acad. Sci. USA., 93:1956-1961 (1996); Barzilai and Shirvan, Cell Mol. Neurobiol., 21:215-235 (2001); Miyazaki and Asunuma, Acta Med Okayama 62:141-150 (2008)). Human neuroblastoma SH-SY5Y cell is a dopaminergic neuronal cell line that has been used as an in vitro model for the study of Parkinson's disease (Gomez-Santos et al., J. Neurosci. Res. 73:341-350 (2003); Jiang et al., Hum Mol Genet 13:1745-1754 (2004); Jiang et al., Synapse 62:797-802 (2008)). High concentrations of dopamine induce death in SH-SY5Y cells mimicking the death of nigral dopaminergic neurons caused by excessive exogenously administered or endogenously produced dopamine (Barzilai and Shirvan, Cell Mol. Neurobiol., 21:215-235 (2001); Miyazaki and Asunuma, Acta Med Okayama 62:141-150 (2008); Gomez-Santos et al., J. Neurosci. Res. 73:341-350 (2003)). This model of dopamine-induced cell death in SH-SY5Y cells was used to study the anti-inflammation actions of des-aspartate-angiotensin I. FIG. 15 shows that des-aspartate-angiotensin I significantly attenuated the death of SH-SY5Y cells caused by high concentration of dopamine. Maximum attenuation occurred at a concentration range of $10^{-10}$ to $10^{-12}$ M des-aspartate-angiotensin I.

e. Glucose-Induced Pancreatic Beta-TC-6 Cell Death

High glucose concentration induces formation of ROS, which damage and kill cells including pancreatic β cells (Nishikawa et al., Nature 404:787-790 (2006); Du et al., Free Radic. Biol. Med., 35:1491-1499 (2003); Robertson and Harmon, Free Radic. Biol. Med. 41:177-184 (2006)). Pancreatic beta TC-6 cells, an insulin-secreting cell line, which are responsive to glucose and glucagon-like peptide-1 (Poitout et al., Diabetes Metab. 22:7-14 (1996); Masur et al., Mol. Endocrinol. 19:1373-1382 (2005)) were used to study the protective action of des-aspartate-angiotensin. FIG. 16 shows that des-aspartate-angiotensin I significantly attenuated the death of pancreatic beta TC-6 cells cause by high concentration of glucose. Maximum attenuation occurred at a concentration of $10^{-12}$ M.

f. LPS-Induced Superoxide and E-Selection Production in A549 Human Lung Epithelial Cells As described in Example 5, superoxide is one of the earlier mediators of inflammation that promote the formation of adhesion molecules (see also the skeletal muscle damage study described above) and infiltration of leucocytes. In this study, LPS, the toxic and inflammatory cellular product of pathogenic gram negative bacteria, was used as an inflammatory stimulus. As several gram negative bacteria (*Hemophilus influenzae, Klebsiella pneumoniae, Legionella pneumophila, Pseudomonas aeruginosa*) specifically infect the human lung, a human lung epithelial cell line, A549, was used. Unlike HUVEC, which was susceptible to the auto-produced superoxide in response to LPS (Simon and Fernandez, J Hypertens 27:1202-1216 (2009)) the superoxide produced by A549 cells had no effect on itself. FIG. 17 shows that LPS concentration-dependently induced the production of superoxide in A549 cell and DAA-I concentration-dependently attenuated the production of superoxide induced by the maximum effective concentration of LPS. The LPS-induced expression of E-selection in A549 cells was also concentration-dependently attenuated by DAA-I (FIG. 18). In both experiments, the maximum effective concentration DAA-I had no effect on the basal level of superoxide or E-selectin.

g. Cancer

That inflammation plays a role in the development of cancer has long been appreciated (Balkwill and Mantovani, Lancet 357:539-645 (2001); Lu et al., Mol. Cancer Res., 4:221-233 (2006); Borello et al., Cancer Lett., 267:262-270 (2009)), and recent studies show a relationship between inflammation and tumor metastasis (Wu and Zhou, Cell Cycle 8:3267-3273 (2009)). In the present study, the effect of des-aspartate-angiotensin I on the development and metastasis of B16-F10 melanoma cells in C57BL/6J mice was investigated. This protocol is an adaptation of the method described by Ren et al. (Stem Cell 26:2332-2338 (2008)) where melanoma cells grow and metastasize in the fully immunocompetent C57BL/6J mouse. The melanoma cells were cultured in DMEM containing 100 U/ml penicillin, 100 μg/ml streptomycin, and 10% fetal calf serum in a 25 cm² flask. Upon confluence, the cells were dislodged with trypsinized PBS, quenched with DMEM and centrifuged (250 g for 8 minutes). The cells were finally re-suspended in PBS and counted and prepared as solution containing 250 cells in 10 μl PBS for administration to mice. Each mouse was anaesthetized with avertin and its abdomen surgically opened up to expose the liver. Melanoma cell preparation was intra-hepatically administered (into the largest lobe) and the abdomen was stitched up using surgical thread. Following this, animals were orally administered 150 nmole/kg/day des-aspartate-angiotensin I for 19 days. Control animals were similarly administered vehicle (water). Animals were killed on the 20$^{th}$ day and their abdomens opened up to expose the liver. The administered melanoma cells developed in the liver as colonies of various sizes. It was also noted that metastatic melanoma cells occurred in abdominal lymphatic system of some animals. Table 3 shows that des-aspartate-angiotensin I attenuated the growth of melanoma cells in liver and abdominal lymphatics of mice, and seven out of ten animals were without tumor growth in the des-aspartate-angiotensin I treated group as compared to four out of ten animals in the control group.

TABLE 3

Effect of des-aspartate-angiotensin I on growth of intra-hepatic administered melanoma cells in mice

| Treatment | n | No. of mice with tumor growth in liver | No. of mice with tumor growth in liver and abdominal lymphatics | No. of mice with no tumor growth |
|---|---|---|---|---|
| Des-aspartate-angiotensin I | 10 | 4 | 2 | 6 |
| Vehicle (water) | 10 | 6 | 5 | 4 |

An in vitro study was carried out to investigate the effects of DAA-I on cell growth and heat shock protein 90 (Hsp90) expression in melanoma cells. B16-F10 melanoma cells were grown to confluence in 25 cm$^2$ flask. The cells were rinsed, trypsinized and seeded into 6-well plates at a density of 8×10$^4$ cells per well. The cells were grown overnight in 10% serum medium, and attained about 80% confluence. The growth medium was changed to one that contained 2% serum, followed by addition of various doses of DAA-I ($10^{-6}$ M to $10^{-20}$ M). The cells were incubated for 24 hours, after which cells were used either for cell viability assay or Hsp90 determination. Cell viability was assayed by staining with 3-(4,5-Dimethylthiazol-2-yl)-2,5-diphenyltetrazolium bromide (MTT; Sigma-Aldrich, St. Louis, Mo.). Briefly, the cells were incubated with 0.5 mg/ml MTT for approximately 1 h at 37° C. in the dark. The medium was aspirated and formazan products formed in viable cells were solubilized with 100 μl dimethylsulfoxide. Viability was quantified by spectrophotometry at 570 nm absorbance using a 96-well plate reader. Hsp90 was determined by Western blotting. Briefly, cells were subjected to lysis buffer (50 mM HEPES/NaOH (pH 7.5), 150 mM NaCl, 2 mM EDTA, 10% glycerol, 10 mM NaF, 2 mM Na$_4$VO$_4$, 1 mM phenylmethylsulfonylfluoride and 10 mM Na$_4$P$_2$O$_7$) for 1 h at 4° C. The protein concentration of the lysate was quantified and 20 μg of protein lysate were then resolved through SDS-PAGE, and probed with Hsp 90 and actin antibodies for western blot analysis. Goat-anti-Hsp90 (1:400 dilution) and mouse-anti-actin (1:4000 dilution) primary antibodies were used. Anti-goat-HRP conjugated (1:20000 dilution) and anti-mouse-HRP conjugated (1:20000 dilution) secondary antibodies were used, respectively. Autoradiography was carried using CL-XPosure film (Thermo Scientific, IL), with exposure time of 15 s to 10 min. The average band intensity was quantified by optical density using Bio-Rad Quantity 1 software. FIG. 19 shows that DAA-I attenuated the growth of melanoma cells at concentrations of $10^{-10}$ to $10^{-14}$ M. The cellular content of Hsp90 was similarly attenuated at these concentrations of the peptide. The in vitro data indicate that des-aspartate-angiotensin I exerts its anti-cancer action by attenuating the production of Hsp90 in melanoma cells. Hsp90 has recently been shown to promote melanoma cell growth and Hsp90 antibodies or inhibitors block cell motility and invasion in vitro and metastasis in vivo (Tsutsumi and Neckers, Cancer Sce. 98:1536-1539 (2007)).

Example 10

Hypoglycemic Action of Tyr-Ile-His-Pro-Phe (SEQ ID NO: 1), Ile-His-Pro-Phe (SEQ ID NO: 2), Val-Tyr The C57BL/6J mice are sensitive to metabolic manipulation (Prarekh et al. Metabolism 47:1089-1096 (1998); Opara et al., J. Nutr., 126:273-279 (1996), Collins et al., Physiol. Behav. 81:243-248 (2004)), and des-aspartate-angiotensin I was surprisingly found to exert hypoglycemic action in this euglycemic animal (Sim et al., Endocrinoogy 148:5925-5932 (2008)). This euglycemic animal model was used to test the hypoglycemic action of three metabolites of des-aspartate-angiotensin I, namely: Tyr-Ile-His-Pro-Phe (SEQ ID NO: 1), Ile-His-Pro-Phe (SEQ ID NO: 2), and Val-Tyr. Table 4 shows that the three metabolites exerted significant hypoglycemic action in this euglycemic animal.

TABLE 4

Hypoglycemic action of metabolites of des-aspartate-angiotensin I

| Metabolite | Serum Glucose Concentration (mM) at 30 min Metabolite of Oral Glucose Tolerance Test |
|---|---|
| 0 (vehicle) | 17.45 ± 0.78 |
| Tyr-Ile-His-Pro-Phe (SEQ ID NO: 1) (400 nmole/kg) | *12.4 ± 0.8 |
| Ile-His-Pro-Phe (SEQ ID NO: 2) (400 nmole/kg) | *13.0 ± 0.72 |
| Val-Tyr (400 nmole/kg) | *11.39 ± 1.12 |

Animals were orally administered (by gavage) 200 nmole/kg/day for 14 days. Oral glucose tolerance was performed after an overnight fast.
*Significantly different from vehicle value While this invention has been particularly shown and described with references to example embodiments thereof, it will be understood by those skilled in the art that various chances in form and details may be made therein without departing from the scope of the invention encompassed by the appended claims. Furthermore, certain terminology has been used for the purposes of descriptive clarity, and not to limit the present invention. The embodiments and preferred features described above should be considered exemplary, with the invention being defined by the appended claims.

What is claimed is:

1. A method for treatment of malignant and/or invasive growth, at least one tumor, tumor metastasis or cancer in a subject comprising the following steps:
   (a) identifying a subject having malignant and/or invasive growth, at least one tumor, tumor metastasis or cancer; and
   (b) administering to the identified subject an effective amount of des-aspartate-angiotensin I or its derivatives, whereby the agonistic effect of the des-aspartate-angiotensin I and/or its derivatives on the angiotensin AT1 receptor results in the production of prostaglandins by COX1, which ameliorate or cure the malignant and/or invasive growth, at least one tumor, tumor metastasis or cancer.

2. The method according to claim 1, wherein the des-aspartate-angiotensin I or its derivatives is administered in conjunction with at least one pharmaceutical agent.

3. The method according to claim 2, wherein the at least one pharmaceutical agent is a type of stem cell.

4. The method according to claim 2, wherein the at least one pharmaceutical agent is a chemotherapeutic agent.

5. The method according to claim 2, wherein the at least one pharmaceutical agent is an immunotherapeutic agent.

6. The method according to claim 1, wherein the method also includes an additional step of identifying that the subject also suffers from inflammatory diseases and pathologies or diseases that are inflammatory in nature.

7. The method according to claim 1, wherein the malignant and/or invasive growth, at least one tumor, tumor metastasis or cancer is on skin tissue.

8. The method according to claim 1, wherein the malignant and/or invasive growth, at least one tumor, tumor metastasis or cancer is melanoma.

9. The method according to claim 1, wherein the effective amount of des-aspartate-angiotensin I or its derivatives is at least 150 nmole/kg/day.

10. The method according to claim 1, wherein the effective amount of des-aspartate-angiotensin I or its derivatives is between 10 mg and 100 mg per subject per day.

11. The method according to claim 1, wherein the effective amount of des-aspartate-angiotensin I or its derivatives attenuates the expression of HSP-90 in tissues or blood of treated patients.

12. The method according to claim 1, wherein the des-aspartate-angiotensin I or its derivatives is administered following or concurrent with radiation therapy.

13. The method according to claim 1, further comprising administering the effective amount of des-aspartate-angiotensin I or its derivatives for at least once a day for at least 19 days.

14. The method according to claim 13, wherein the effective amount of des-aspartate-angiotensin I or its derivatives is at least 150 nmole/kg/day.

15. The method according to claim 13, wherein the malignant and/or invasive growth, at least one tumor, tumor metastasis or cancer is on skin tissue.

16. The method according to claim 13, wherein the malignant and/or invasive growth, at least one tumor, tumor metastasis or cancer is melanoma.

17. The method according to claim 13, wherein the effective amount of des-aspartate-angiotensin I or its derivatives is between 10 mg and 100 mg per subject per day.

18. The method according to claim 13, wherein the effective amount of des-aspartate-angiotensin I or its derivatives attenuates the expression of HSP-90 in tissues or blood of treated patients.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Tyr Ile His Pro Phe
1               5

<210> SEQ ID NO 2

```
<211> LENGTH: 4
<212> TYPE: PRT
<213> ORGANISM: Homo sapiens

<400> SEQUENCE: 2

Ile His Pro Phe
1
```